United States Patent [19]

Hardy et al.

[11] 4,198,406

[45] Apr. 15, 1980

[54] CARBAMOYL HETEROCYCLICTHIO CEPHALOSPORINS AND PHARMACEUTICAL COMPOSITIONS FORMULATED THEREWITH

[75] Inventors: Kenneth D. Hardy, Horsham; George Burton, Sutton, both of England

[73] Assignee: Beecham Group Limited, Great Britain

[21] Appl. No.: 835,218

[22] Filed: Sep. 21, 1977

Related U.S. Application Data

[62] Division of Ser. No. 743,852, Nov. 22, 1976.

[30] Foreign Application Priority Data

Nov. 27, 1975 [GB] United Kingdom ............... 48719/75
Apr. 13, 1976 [GB] United Kingdom ............... 14952/76

[51] Int. Cl.$^2$ .................. A61K 31/545; C07D 501/36
[52] U.S. Cl. .................................. 424/246; 544/26; 544/27; 424/272
[58] Field of Search ................... 544/27, 26; 424/246

[56] References Cited

U.S. PATENT DOCUMENTS

| | | | |
|---|---|---|---|
| 3,956,292 | 5/1976 | Cooper | 544/27 |
| 3,994,886 | 11/1976 | Crooij et al. | 544/27 |
| 4,024,137 | 5/1977 | Cook et al. | 544/28 |
| 4,025,626 | 5/1977 | Berges | 544/27 |
| 4,034,092 | 7/1977 | Berges | 544/26 |
| 4,048,311 | 9/1977 | Berges | 544/27 |
| 4,049,651 | 9/1977 | Breuer et al. | 544/26 |
| 4,086,422 | 4/1978 | Breuer et al. | 544/27 |
| 4,101,661 | 7/1978 | Kaltenbronn et al. | 544/27 |
| 4,103,008 | 7/1978 | Toshiyasu et al. | 544/26 |
| 4,110,327 | 8/1978 | Saikawa et al. | 544/28 |
| 4,117,126 | 9/1978 | Yamada et al. | 544/27 |

FOREIGN PATENT DOCUMENTS 2514019 10/1975 Fed. Rep. of Germany.

*Primary Examiner*—David Wheeler
*Attorney, Agent, or Firm*—Jacobs & Jacobs

[57] ABSTRACT

Novel cephalosporin compounds, process of preparation thereof, intermediates useful in the preparation of the cephalosporins, pharmaceutical compositions formulated therefrom for administration and combinations of the cephalosporins in pharmaceutical composition form with clavulanic acid. The cephalosporin compounds are characterized by a 5-membered nitrogen-containing ring in the group in the 3-position of the sulphur-containing ring.

19 Claims, No Drawings

CARBAMOYL HETEROCYCLICTHIO CEPHALOSPORINS AND PHARMACEUTICAL COMPOSITIONS FORMULATED THEREWITH

CROSS-REFERENCE

This is a division of Ser. No. 743,852 filed Nov. 22, 1976.

This invention relates to cephalosporin compounds, to a process for their preparation and to intermediates useful in their preparation.

According to the present invention, there is provided a compound of formula (I) or a pharmaceutically acceptable salt or ester thereof:

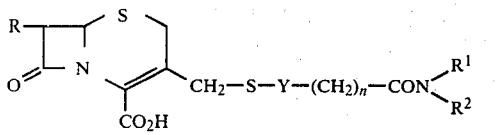

wherein R represents an organic acylamino group, a group of formula:

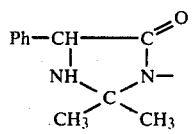

or a group of formula:

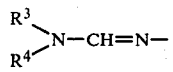

wherein $R^3$ and $R^4$ each represent a $C_{1-3}$ alkyl group or $R^3$ and $R^4$ taken together with the nitrogen atom to which they are attached form a monocyclic ring;

Y represents a 5-membered nitrogen-containing ring;

n is zero or 1; and $R^1$ and $R^2$ are the same or different and each is hydrogen or a $C_{1-6}$ alkyl group.

The compounds of the present invention include the pharmaceutically acceptable non-toxic esters of compound (I). Suitable esters include those which hydrolyse readily in the human body to produce the parent acid, for example acyloxyalkyl esters such as acetoxymethyl, pivaloyloxymethyl, α-acetoxyethyl, α-acetoxybenzyl and α-pivaloyloxyethyl esters; alkoxycarbonyloxyalkyl esters, such as ethoxycarbonyloxymethyl and α-ethoxycarbonyloxyethyl; and lactone, thiolactone and dithiolactone esters, i.e. ester groups of formula:

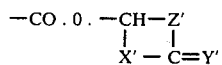

wherein X' and Y' are oxygen or sulphur and Z' is an ethylene group or a 1,2-phenylene group optionally substituted by lower-alkoxy, halogen or nitro.

Preferred ester groups are the phthalide and 5,6-dimethoxyphthalide esters.

Suitable salts of the compound of formula (I) include metal salts, e.g. aluminium, alkali metal salts such as sodium or potassium, alkaline earth metal salts such as calcium or magnesium, and ammonium or substituted ammonium salts, for example those with lower alkylamino such as tri-ethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bis-dehydroabietylethylenediamine, or bases of the pyridine type such as pyridine, collidine or quinoline, or other amines which have been used to form salts with benzylpenicillin.

When the compounds of formula (I) contain a free amino group, pharmaceutically acceptable acid addition salts of such a compound are also included within this invention. Suitable acid addition salts of the compounds of formula (I) include, for example, inorganic salts such as the sulphate, nitrate, phosphate and borate; hydrohalides e.g. hydrochloride, hydrobromide and hydroiodide; and organic acid addition salts such as acetate, oxalate, tartrate, maleate, citrate, succinate, benzoate, ascorbate, methanesulphonate and p-toluenesulphonate, trifluoroacetate.

When R is an organic acylamino group, specific examples include any of the acylamino side chains found in known antibacterially active penicillins and cephalosporins. It has been found over the years that by varying the identity of the 7-acylamino group of ceph-3-ems, the spectrum and/or level of antibacterial activity of any given ceph-3-em can be modified. Similarly, in the present case, for any given value of the 3-substituent in formula (I) a very large number of 7-acylamino groups can be introduced, producing a range of compounds of widely differing spectra and levels of activity. In general, however, whatever the identity of the acylamino group R, the compounds of formula (I) possess some activity and those who are familiar with the cephalosporin art will be aware of the range of acylamino groups R which may be introduced.

In general therefore, R in formula (I) may be any of the organic acylamino groups which are present in the reported natural and semi-synthetic penicillins and cephalosporins. The acyl portion may be, for example, one of the following groups of formulae (i)–(iv):

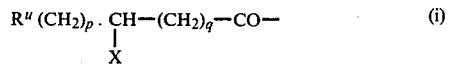

wherein $R^u$ represents hydrogen, alkyl, cycloalkyl (especially $C_3$ to $C_6$ cycloalkyl), alkenyl, cycloalkenyl, aryl (especially phenyl or substituted phenyl) or heterocyclic; X represents hydrogen, halogen, carboxy, esterified carboxy, azide, amino, substituted amino (including ureido, substituted ureido, for example acyl ureido, guanidino and substituted guanidino groups), a triazolyl group, a tetrazolyl group, a cyano group, an acyloxy group (e.g. formyloxy or lower alkanoyloxy group) or an esterified hydroxy group; and p and q each separately represent 0,1,2 or 3.

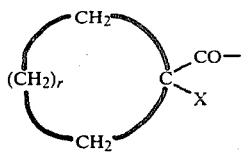 (ii)

wherein r is an integer from 1 to 4 and X is as defined in (i) above.

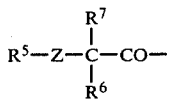 (iii)

wherein $R^5$ is an alkyl, aralkyl, aryl (especially phenyl or substituted phenyl group), cycloalkyl (especially a $C_3$ to $C_6$ cycloalkyl or substituted cycloalkyl group), cycloalkenyl (especially a cyclohexenyl or cyclohexadienyl group) or a heterocyclic group (especially a thienyl or pyridyl group); $R^6$ and $R^7$ are each hydrogen, lower alkyl, phenyl, benzyl or phenylethyl groups; and Z is oxygen or sulphur.

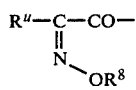 (iv)

where $R^8$ is a lower alkyl group and $R^u$ is as defined above.

Specific examples of organic acylamino groups R which may be present in the compounds of this invention include 2-thienylacetamido, 3-thienylacetamido, phenylacetamido, 2-hydroxyphenylacetamido, 2-aminophenylacetamido, 4-pyridylacetamido, 2-amino-2-(4-hydroxyphenyl)acetamido, 2-methoxyimino-2-fur-2'-ylacetamido, 2-carboxy-2-thien-3-ylacetamido, 2-carboxy-2-phenylacetamido, 2-carboxy-2-(4-hydroxyphenyl)acetamido, and 1-tetrazolylacetamido, but other acyl groups are specifically exemplified in the Examples later in this specification.

One class of compounds of formula (I) are those wherein the acyl portion of the group R is of formula (i) wherein p and q are zero, $R^u$ represents a furyl, thienyl, cycloalkyl, cycloalkenyl, or phenyl group, or a phenyl group substituted by hydroxy, halogen, nitro, lower alkyl, lower alkoxy, amino, or carboxy; and X represents hydrogen, hydroxy, amino, carboxy, salted carboxy, esterified carboxy, ureido, or acylureido.

Within this class, suitable groups $R^u$ include 2- and 3-furyl, 2- and 3- thienyl, cyclopropyl, cyclobutyl, cyclopentyl, cyclohexyl, cyclobutenyl, cyclopentenyl, cyclohexenyl, cyclohexa-1, 4-dienyl, phenyl, 4-hydroxyphenyl, 3-chloro-4-hydroxyphenyl, 3,4-dihydroxyphenyl, 4-methoxyphenyl. Preferably $R^u$ is a 2- or 3- thienyl, phenyl or 4-hydroxyphenyl group.

The group X may be, for example, hydrogen, esterified carboxy, ureido or acylureido.

Preferably the group X is hydrogen, amino, carboxy or acylureido. When X is an acylureido group, it may be of the formula:

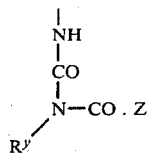

wherein $R^y$ is hydrogen or a lower alkyl or benzyl group and Z is an organic radical containing up to 20 carbon atoms, or $R^y$ and Z together with the carbon and nitrogen atoms to which they are attached form a 5,6 or 7-membered ring. Z may be for example $C_{1-10}$ alkyl; $C_{1-10}$ alkenyl; aralkyl or aralkenyl in which the alkyl and alkenyl radicals are $C_{1-10}$ and the aryl radicals are phenyl, thienyl, furyl, pyridyl or substituted phenyl wherein the substituents are selected from $C_{1-3}$ alkyl, $C_{1-3}$ alkoxy, halogen, nitro and amino groups; $C_{1-10}$ alkoxy, $C_{5-7}$ cycloalkoxy; $C_{1-10}$ alkylamino; functionally substituted $C_{1-10}$ alkyl wherein the functional substituent is, for example, $C_{1-3}$ alkylthio, $C_{1-3}$ alkoxy or phenoxy.

Preferably Z is $C_{1-6}$ alkyl, or $C_{1-6}$ alkenyl, either of which may be substituted with a phenyl, halophenyl or nitrophenyl or Z is a furyl or thienyl group or a phenyl group optionally substituted by up to three halogen, nitro, $C_{1-3}$ alkyl or $C_{1-3}$ alkoxy groups; or $R^y$ and Z together with the carbon and nitrogen atoms to which they are attached form a 5-, 6-, or 7-membered ring.

Suitably $R^y$ is $C_{1-3}$ alkyl, preferably methyl.

The group Z may be, for example, methyl, ethyl, n- or isopropyl, n-, sec- or tert-butyl, prop-2-enyl, but-2-enyl, benzyl, 2-phenylethyl, 3-phenylpropyl, p-chlorobenzyl, 2-(p-chlorophenyl)-ethyl, 2-phenylethenyl, 2-(p-nitrophenyl)ethenyl, 2-(p-chlorophenyl) ethenyl, phenyl, 2-methoxyphenyl, 2-chlorophenyl, 2-methoxyphenyl, 3,4,5-trimethoxyphenyl, 4-nitrophenyl, 2-methylphenyl, 4-methylphenyl, furyl, thienyl.

When $R^y$ and Z are taken together with the carbon and nitrogen atoms to which they are joined, the ring which is formed may be, for example, one of the following:

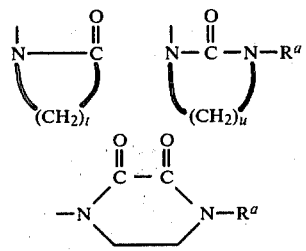

in which t is an integer from 3 to 5 and u is an integer from 2 to 4 and $R^a$ is hydrogen, $C_1$–$C_3$ alkyl, $C_1$–$C_3$ acyl, or $C_1$–$C_3$ alkylsulphonyl. Preferably the ring formed is imidazolidin-2-on-1-yl, 3-acetyl-imidazolidin-2-on-1-yl, 3-methylsulphonylimidazolidin-2-on-1-yl, hexahydroazepin-2-on-1-yl or 4-ethyl-2,3-dioxo-1-piperazino.

Preferred values for the group Z are phenyl, isopropyl and 2-phenylethyl.

Specific acylureido groups for group X include:
N-benzoyl-N-methylureido;
N-(2-chlorobenzoyl)-N-methylureido;
N-(2-furoyl)-N-methylureido;
N-isobutyryl-N-methylureido;

N-(3-thienoyl)-N-methylureido;
N-(3-furoyl)-N-methylureido;
N-cinnamoyl-N-methylureido;
imidazolidin-2-on-1-ylcarbonylamino; and
4-ethyl-2,3-dioxo-1-piperazinocarbonylamino.

When X is a carboxylic acid derivative it may be a group of formula —$CO_2R^9$ wherein $R^9$ is hydrogen, a pharmaceutically acceptable salting ion, an in vivo hydrolysable ester radical, or an alkyl, cycloalkyl, alkenyl, alkynyl, aryl, aralkyl or heterocyclic group, any of which may be substituted.

Suitable salting ions and in vivo hydrolysable ester radicals are discussed above with respect to the cephem 4-carboxylic acid group.

In addition the group $R^9$ may be an alkyl, cycloalkyl, alkenyl, alkynyl, aryl, aralkyl or heterocyclic group any of which may be substituted. Suitable such groups include:

(a) alkyl especially lower alkyl such as methyl, ethyl, n- and iso-propyl, n-, sec-, iso- and tert-butyl, pentyl;

(b) substituted lower alkyl wherein the substituent is at least one of: chloro, bromo, fluoro, nitro, carbo (lower alkoxy), lower alkanoyl, lower alkoxy, cyano, (lower)alkylmercapto, (lower)alkylsulphinyl, (lower) alkylsulphonyl, 1-indanyl, 2-indanyl, furyl, pyridyl, 4-imidazolyl, phthalimido, azetidino, aziridino, pyrrolidino, piperidino, morpholino, thiomorpholino, N-(lower alkyl) piperazino, pyrrolo, imidazolo, 2-imidazolino, 2,5-dimethylpyrrolidino, 1,4,5,6-tetrahydropyrimidino, 4-methylpiperidino, 2,6-dimethylpiperidino, alkylamino, dialkylamino, alkanoylamine, alkylanilino, or substituted alkylanilino wherein the substituent is chloro, bromo, lower alkyl or lower alkoxy;

(c) cycloalkyl and (lower alkyl) substituted cycloalkyl having from 3 to 7 carbon atoms in the cycloalkyl moiety and (2,2-di(lower alkyl)-1,3-dioxolon-4-)methyl;

(d) alkenyl having up to 8 carbon atoms;

(e) alkynyl having up to 8 carbon atoms;

(f) aryl groups such as phenyl and substituted phenyl wherein the substituent is at least one of chloro, bromo, fluoro, lower alkyl, lower alkoxy, lower alkanoyl, carbo(lower)alkoxy, nitro, or di(lower-)alkyl amino; and groups of formula:

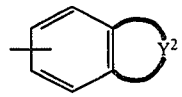

or

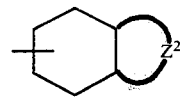

wherein $Z^2$ is lower alkylene such as $(CH_2)_3$— or —$(CH_2)_4$—, and substituted derivatives thereof wherein the substituent is methyl, chloro or bromo;

(g) aralkyl groups such as benzyl or substituted benzyl wherein the substituent is chloro, bromo, fluoro, lower alkyl, lower alkoxy, lower alkanoyl, carbo(lower)alkoxy, nitro, or di(lower)alkylamino;

(h) heterocyclic groups such as: furyl, quinolyl, methylsubstituted quinolyl, phenazinyl, 1,3-benzodioxolyl, 3-(2-methyl-4-pyronyl), 3-(4-pyronyl) or N-(methylpyridyl);

(j) other hydrocarbyl groups such as: ac-indanyl and substituted derivatives thereof wherein the substituent is methyl, chloro or bromo; ac-tetrahydronaphthyl and substituted derivatives thereof wherein the substituent is methyl, chloro or bromo; benzohydroyl, trityl, cholesteryl, bicyclo[4.4.0]decyl.

Preferred groups for $R^1$ include lower alkyl, benzyl, phthalidyl, indanyl, phenyl, mono-, di-, and tri- (lower)-alkyl substituted phenyl such as o-, m- or p-methylphenyl, ethylphenyl, n- or iso-propylphenyl, n-, sec-, iso- or t-butylphenyl.

Examples of the group Y include diazolyl, triazolyl, tetrazolyl, thiazolyl, thiadiazolyl, thiatriazolyl, oxazolyl and oxadiazolyl groups.

Suitable groups Y include oxadiazolyl, thiadiazolyl and triazolyl.

A preferred group Y is tetrazolyl.

The integer n is preferably equal to 1.

Suitable groups $R^1$ and $R^2$ include hydrogen, methyl, ethyl, n- and iso-propyl, n-, iso-, sec- and t-butyl. Preferably $R^1$ and $R^2$ are both hydrogen.

Thus, examples of the moiety —Y—$(CH_2)_n$—$CONR^1R^2$ include:
2-carbamoylmethyl-1,3,4-oxadiazol-5-yl;
2-carbamoyl-1,3,4-oxadiazol-5-yl;
1-carbamoylmethyl-1H-tetrazol-5-yl;
1-(N-methylcarbamoylmethyl)-1H-tetrazol-5-yl;
1-(N,N-dimethylcarbamoylmethyl)-1H-tetrazol-5-yl;
2-carbamoylmethyl-1,3,4-thiadiazol-5-yl;
2-carbamoylmethyl-1,3,4-triazol-5-yl.

One preferred sub-class of cephalosporins included within this invention is of formula (IV) or a pharmaceutically acceptable salt or ester thereof:

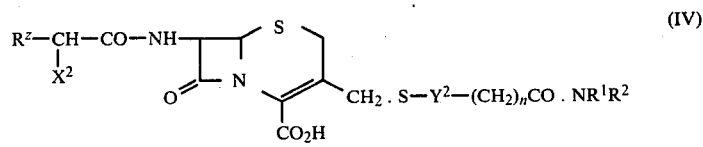

(IV)

wherein $X^2$ is amino or acylureido and $Y^2$ is an oxadiazole thiadiazole or tetrazole group, and $R^z$ is phenyl or 4-hydroxyphenyl.

Specific compounds falling within formula (IV) include:
7-[D-α-(3-benzoyl-3-methylureido)-phenylacetamido]-3-(2-carbamoylmethyl-1,3,4- wherein $Y^2$ is:
—CH=CH—O—
—CH=CH—S—
—$CH_2$—$CH_2$—S—
—CH=N—CH=CH—
—CH=CH—CH=CH—
—CO—CH=CH—CO— or
—CO—CO—CH=CH—;

oxadiazol-5-ylthio)methylceph-3-em-4-carboxylic acid;

7-[D-α-(3-benzoyl-3-methylureido)-phenylacetamido]-3-(2-carbamoyl-1,3,4-oxadiazol-5-ylthio)methylceph-3-em-4-carboxylic acid;

7-[D-α-(3-benzoyl-3-methylureido)-phenylacetamido]-3-(1-carbamoylmethyl-1H-tetrazol-5-ylthio)methylceph-3-em-4-carboxylic acid;

7-(D-α-aminophenylacetamido)-3-(2-carbamoylmethyl-1,3,4-oxadiazol-5-ylthio)methylceph-3-em-4-carboxylic acid;

7-(D-α-aminophenylacetamido)-3-(2-carbamoyl-1,3,4-oxadiazol-5-ylthio)methylceph-3-em-4-carboxylic acid;

7-(D-α-aminophenylacetamido)-3-(1-carbamoylmethyl-1H-tetrazol-5-ylthio)methylceph-3-em-4-carboxylic acid;

7-[D,α-(3-benzoyl-3-methylureido)-phenylacetamido]-3-(2-carbamoylmethyl-1,3,4-thiadiazol-5-ylthio)methylceph-3-em-4-carboxylic acid;

7-[D,α-(3-2′-chlorobenzoyl-3-methylureido)-phenylacetamido]-3-(1-carbamoylmethyl-1H-tetrazol-5-ylthio)methylceph-3-em-4-carboxylic acid;

7-[D-α-(3-2′-furoyl-3-methylureido)-phenylacetamido]-3-(1-carbamoylmethyl-1H-tetrazol-5-ylthio)methylceph-3-em-4-carboxylic acid;

7-[D-α-(3-isobutyryl-3-methylureido)-phenylacetamido]-3-(1-carbamoylmethyl-1H-tetrazol-5-ylthio)methylceph-3-em-4-carboxylic acid;

7-[D-α-(3-methyl-3,3′-thienoylureido)-phenylacetamido]-3-(1-carbamoylmethyl-1H-tetrazol-5-ylthio)methylceph-3-em-4-carboxylic acid;

7-[D-α-(3-3′-furoyl-3-methylureido)-phenylacetamido]-3-(1-carbamoylmethyl-1H-tetrazol-5-ylthio)methylceph-3-em-4-carboxylic acid;

7-(D,α-amino-4-hydroxyphenylacetamido)-3-(1-carbamoylmethyl-1H-tetrazol-5-ylthio)methylceph-3-em-4-carboxylic acid;

7-(D,α-amino-4-hydroxyphenylacetamido)-3-(2-carbamoylmethyl-1,3,4-thiadiazol-5-ylthio)methylceph-3-em-4-carboxylic acid;

7-[D,2-(4-ethyl-2,3-dioxopiperazino-1-carbonylamino)-2-phenylacetamido]-3-(1-carbamoylmethyl-1H-tetrazol-5-ylthio)methylceph-3-em-4-carboxylic acid;

Another preferred class of compounds is of formula (V) or a pharmaceutically acceptable salt or ester thereof:

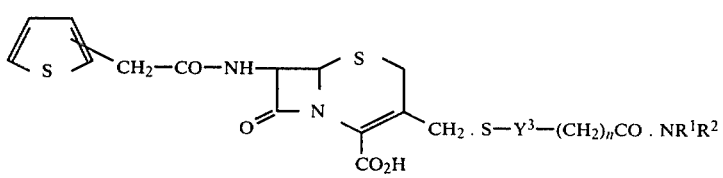

(V)

wherein $Y^3$ is a tetrazole, thiadiazole, or oxadiazole group.

Specific compounds falling within formula (V) include:

7-(thien-2-ylacetamido)-3-(2-carbamoylmethyl-1,3,4-oxadiazol-5-ylthio)methylceph-3-em-4-carboxylic acid;

7-(thien-2-ylacetamido)-3-(2-carbamoyl-1,3,4-oxadiazol-5-ylthio)methylceph-3-em-4-carboxylic acid;

7-(thien-2-ylacetamido)-3-(1-carbamoylmethyl-1H-tetrazol-5-ylthio)methylceph-3-em-4-carboxylic acid;

7-(thien-2-ylacetamido)-3-(carbamoylmethyl-1,3,4-thiadiazol-5-ylthio)methylceph-3-em-4-carboxylic acid;

7-(thien-2-ylacetamido)-3-[1-(N-methylcarbamoylmethyl)-1H-tetrazol-5-ylthio]methylceph-3-em-4-carboxylic acid;

7-(thien-2-ylacetamido)-3-[1-(N,N-dimethylcarbamoylmethyl)-1H-tetrazol-5-ylthio]methylceph-3-em-4-carboxylic acid;

7-(thien-3-ylacetamido)-3-(1-carbamoylmethyl-1H-tetrazol-5-ylthio)-methylceph-3-em-4-carboxylic acid.

A particularly advantageous sub-class of compounds within the invention is of formula (VA) or a pharmaceutically acceptable salt or ester thereof:

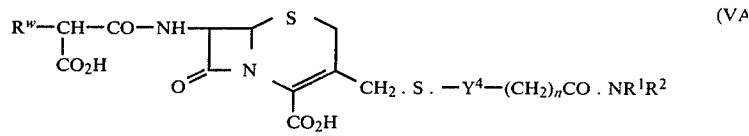

(VA)

wherein $Y^4$ is a tetrazole, thiadiazole, oxadiazole or triazole group and $R^w$ is 2- or 3-thienyl, phenyl, 4-hydroxyphenyl, or 4-methoxyphenyl.

Within formula (VA), advantageously the group $R^w$ is 2- or 3-thienylphenyl or 4-hydroxyphenyl, preferably 3-thienyl. Suitable $Y^4$ is tetrazole, thiadiazole or oxadiazole.

One specific compound falling within formula (VA) is:

7-(2-carboxy-2-thien-3′-ylacetamido)-3-(1-carbamoylmethyl-1H-tetrazole-5-ylthio)methyl-ceph-3-em-4-carboxylic acid. (i.e., formula (VA), $R^w=3$-thienyl, $Y^4=1$H-tetrazolyl, $n=1$, $R^1=R^2=H$).

Other particular compounds of formula (VA) include:

7-(2-carboxy-2-thien-3′-ylacetamido)-3-(2-carbamoyl-1,3,4-oxadiazol-5-ylthio)methylceph-3-em-4-carboxylic acid;

7-(2-carboxy-2-thien-3′-ylacetamido)-3-(1,N-methylcarbamoylmethyl-1H-tetrazol-5-ylthio)methyl-ceph-3-em-4-carboxylic acid;

7-(2-carboxy-2-thien-3′-ylacetamido)-3-(1,N,N-dimethylcarbamoylmethyl-1H-tetrazol-5-ylthio)methyl-ceph-3-em-4-carboxylic acid;

7-(2-carboxy-2-thien-3'-ylacetamido)-3-(2-carbamoylmethyl-1,3,4-thiadiazol-5-ylthio)methylceph-3-em-4-carboxylic acid;

7-[2-carboxy-2-(4-hydroxyphenyl)acetamido]-3-(1-carbamoylmethyl-1H-tetrazol-5-ylthio)methylceph-3-em-4-carboxylic acid;

7-[2-carboxy-2-(4-methoxyphenyl)acetamido]-3-(1-carbamoylmethyl-1H-tetrazol-5-ylthio)methylceph-3-em-4-carboxylic acid;

7-[2-(4-methylphenoxycarbonyl)-2-thien-3'-ylacetamido]-3-(1-carbamoylmethyl-1H-tetrazol-5-ylthio)methylceph-3-em-4-carboxylic acid;

7-(2-carboxy-2-thien-3'-ylacetamido)-3-(3-carbamoylmethyl-1,2,4-triazol-5-ylthio)methylceph-3-em-4-carboxylic acid.

Other particular compounds of this invention include:

7-(D,2-hydroxy-2-phenylacetamido)-3-(1-carbamoylmethyl-1H-tetrazol-5-ylthio)methylceph-3-em-4-carboxylic acid;

7-(2-methoxyimino-2-fur-2'-ylacetamido)-3-(1-carbamoylmethyl-1H-tetrazol-5-ylthio)methylceph-3-em-4-carboxylic acid.

Compounds of formula (I), salts and esters thereof wherein R is an acylamino may be prepared by reacting a compound of formula (VI) or an N-protected derivative thereof:

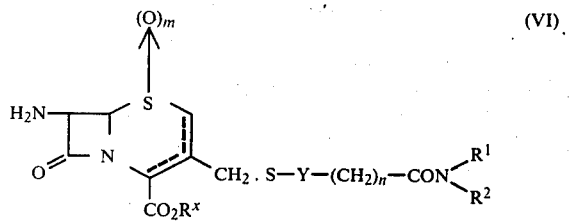 (VI)

wherein $R^x$ is hydrogen or a carboxyl blocking group, m is zero or 1, the dotted line represents a bond in the 2- or 3-position, and Y, n, $R^1$ and $R^2$ are as defined in formula (I), with an N-acylating derivative of an acid of formula (VII):

 (VII)

wherein $R^q$ is an organic acyl group such that R in formula (I) represents $R^qNH-$ and where any reactive groups (such as amino carboxy and hydroxy groups) may be blocked and thereafter, if necessary, carrying out one or more of the following steps:

(i) converting a Δ2 isomer into the desired Δ3 isomer;
(ii) removing any N-protecting groups;
(iii) reducing a sulphoxide compound to form the desired sulphide compound;
(iv) removal of any blocking groups from the group $R^x$ or the acyl side chain;
(v) converting the product to a salt or ester thereof.

Examples of "N-protected derivatives" of compound (VI) include N-silyl and N-phosphorylated derivatives.

By the term "N-silyl derivatives" of compound (VI), we mean the product of reaction of the 7-amino group of compound (VI) with a silylating agent such as a halosilane or a silazane of the formula:

L₃ Si U; L₂ Si U₂; L₃ Si NL₂;
L₃ Si NH Si L₃; L₃ Si.NH.COL; L₃ Si.NH.CO.NH.Si L₃;
L NH.CO.NH.Si L₃;

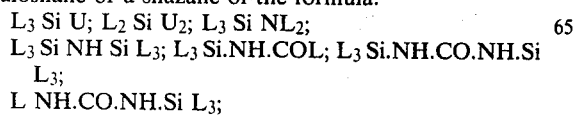

wherein U is a halogen and the various groups L which may be the same or different, each represents hydrogen or alkyl, alkoxy, aryl, or aralkyl. Preferred silylating agents are silyl chlorides, particularly trimethylchlorosilane, and dimethyldichlorosilane.

The term "N-phosphorylated" derivative of compound (VI) is intended to include compounds wherein the 7-amino group of formula (VI) is substituted with a group of formula:

$-P.R_aR_b$ wherein $R_a$ is an alkyl, haloalkyl, aryl, aralkyl, alkoxy, haloalkoxy, aryloxy, aralkyloxy or dialkylamino group, $R_b$ is the same as $R_a$ or is halogen or $R_a$ and $R_b$ together form a ring.

Suitable carboxyl-blocking derivatives of the group $-CO_2R^x$ in formula (V) include salts, esters, and anhydride derivatives of the carboxylic acid. The derivative is preferably one which may readily be cleaved at a later stage of the reaction. Suitable salts include tertiary amine salts, such as those with tri-lower-alkylamines, N-ethylpiperidine, 2,6-lutidine, pyridine, N-methylpyrrolidine, dimethylpiperazine. A preferred salt is with triethylamine.

Suitable ester groups of formula $CO_2R^x$ include the following:

(i) $-COOCR_cR_dR_e$ wherein at least one of $R_c$, $R_d$ and $R_e$ is an electron-donor, e.g. p-methoxyphenyl, 2,4,6-trimethylphenyl, 9-anthryl, methoxy, acetoxy, or fur-2-yl. The remaining $R_c$, $R_d$ and $R_e$ groups may be hydrogen or organic substituting groups. Suitable ester groups of this type include p-methoxybenzyloxycarbonyl, 2,4,6-trimethylbenzyloxy carbonyl, bis-(p-methoxyphenyl)methoxycarbonyl, and 3,5-di-t-butyl-4-hydroxybenzyloxycarbonyl.

(ii) $-COOCR_cR_dR_e$ wherein at least one of $R_c$, $R_d$ and $R_e$ is an electron-attracting group, e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining $R_c$, $R_d$ and $R_e$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) $-COOCR_cR_dR_e$ wherein at least two of $R_c$, $R_d$ and $R_e$ are hydrocarbon such as alkyl e.g. methyl or ethyl, or aryl e.g. phenyl and the remaining $R_c$, $R_d$ and $R_e$ group, if there is one, is hydrogen. Suitable esters of this type include t-butyloxycarbonyl, t-amyloxycarbonyl, diphenylmethoxycarbonyl and triphenylmethoxycarbonyl.

(iv) $-COOR_f$ wherein $R_f$ is adamantyl, 2-benzyloxyphenyl, 4-methylthiophenyl, tetrahydrofur-2-yl, tetrahydropyran-2-yl, pentachlorophenyl;

(v) Silyloxycarbonyl groups obtained by reaction of a silylating agent of the type described above with the carboxylic acid group;

(vi) CO₂P.R$_a$R$_b$, wherein R$_a$ and R$_b$ are as defined above;
(vii) trialkyltin esters;
(viii) oxime esters of formula CO$_2$N=CH.R$_g$ where R$_g$ is aryl or heterocyclic.

The carboxyl group may be regenerated from any of the above esters by usual methods appropriate to the particular R$^x$ group, for example, acid—and base—catalysed hydrolysis, or by enzymically—catalysed hydrolysis. Alternative methods of cleavage include:

reaction with Lewis acids, such as trifluoroacetic acid, formic acid, hydrochloric acid in acetic acid, zinc bromide in benzene and aqueous solutions or suspensions of mercuric compounds. (The reaction with the Lewis acid may be facilitated by addition of a nucleophile such as anisole);

reduction with agents such as zinc/aqueous acetic acid, zinc/formic acid, zinc/lower alcohol, zinc/pyridine, or hydrogen and palladised-charcoal or other supported hydrogenation catalysts; attack by nucleophiles, such as those containing a nucleophilic oxygen or sulphur atom for example alcohol mercaptans and water; oxidative methods, for example, those which involve the use of hydrogen peroxide and acetic acid; and irradiation with light or u.v.

A reactive N-acylating derivative of the acid (VII) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be effected in the presence of an acid binding agent for example tertiary amine (such as triethylamine or dimethylaniline), an inorganic base (such as calcium carbonate or sodium bicarbonate) or an oxirane, which binds hydrogen halide liberated in the acylation reaction. The oxirane is preferably a (C$_{1-6}$)-1,2-alkylene oxide—such as ethylene oxide or propylene oxide. The acylation reaction using an acid halide may be carried out at a temperature in the range $-50°$ to $+50°$ C., preferably $-20°$ to $+30°$ C., in aqueous or non-aqueous media such as aqueous acetone, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (VII) or a salt thereof with a halogenating (e.g. chlorinating or brominating) agent such as phosphorus pentachloride, thionyl chloride or oxalyl chloride.

Alternatively, the N-acylating derivative of the acid (VII) may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric or phosphorous acids), sulphuric acid or aliphatic or aromatic sulphonic acids (such as p-toluenesulphonic acid). The mixed or symmetrical anhydrides may be generated in situ. For example, a mixed anhydride may be generated using N-ethoxycarbonyl-2-ethoxy-1,2-dihydroquinoline. When a symmetrical anhydride is employed, the reaction may be carried out in the presence of 2,4-lutidine as catalyst.

Alternative N-acylating derivatives of acid (VII) are the acid azide, or activated esters such as esters with 2-mercaptopyridine cyanomethanol, p-nitrophenol, 2,4-dinitrophenol, thiophenol, halophenol, including pentachlorophenyl, monomethoxy phenol or 8-hydroxyquinoline; or amides such as N-acylsaccharins or N-acylnaphthalimides; or an alkylidene iminoester prepared by reaction of the acid (VII) with an oxime.

Some activated esters, for example the ester formed with 1-hydroxybenztriazole or N-hydroxysuccinimide, may be prepared in situ by the reaction of the acid with the appropriate hydroxy compound in the presence of a carbodiimide, preferably dicyclohexylcarbodiimide.

Other reactive N-acylating derivatives of the acid (VII) include the reactive intermediate formed by reaction in situ with a condensing agent such as a carbodiimide, for example N,N-diethyl-, dipropyl- or diisopropylcarbodiimide, N,N'-di-cyclohexylcarbodiimide, or N-ethyl-N'-γ-dimethylaminopropylcarbodiimide; a suitable carbonyl compound, for example N,N'-carbonyldiimidazole or N,N'-carbonylditriazole; an isoxazolinium salt, for example N-ethyl-5-phenylisoxazolinium-3-sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline. Other condensing agents include Lewis acids (for example BBr$_3$-C$_6$H$_6$); or a phosphoric acid condensing agent such as diethylphosphorylcyanide. The condensation reaction is preferably carried out in an organic reaction medium, for example methylene chloride, dimethylformamide, acetonitrile, alcohol, benzene, dioxan, or tetrahydrofuran.

With the above route it is preferable to protect any reactive groups in the acyl side-chain prior to the acylation reaction. When the group to be protected is an amino group, any of the amino groups known from the literature on the synthesis of α-aminobenzyl penicillin are suitable.

Examples of protected amino groups include the protonated amino group (NH$^+_3$) which after the acylation reaction can be converted to the free amino group by simple neutralisation; the benzyloxy-carbonylamino group or substituted benzyloxycarbonyl-amino groups which are subsequently converted to NH$_2$ by catalytic hydrogenation; and various groups which after the acylation reaction regenerate the amino group on mild acid hydrolysis, such as t-butyloxycarbonyl group which may be removed by treatment with trifluoroacetic acid, hydrogen chloride, or p-toluenesulphonic acid.

Another example of a protected amino group which may subsequently be converted to NH$_2$ by mild acid hydrolysis include groups of formula (VIII):

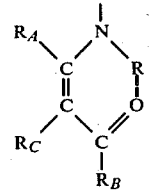

(VIII)

wherein R$_A$ is an alkyl, aralkyl or aryl group, R$_B$ is an alkyl, aralkyl, aryl, alkoxy, aralkoxy or aryloxy group, and R$_C$ is a hydrogen atom or an alkyl, aralkyl, or aryl group, or R$_c$ together with either R$_A$ or R$_B$ completes a carbocyclic ring.

An example of a "protected amino" which can be converted to NH₂ after the N-acylation reaction is the azido group. In this case, the final conversion into NH₂ may be brought about by either catalytic hydrogenation or electrolytic reduction. Alternatively the amino group may be blocked as the nitro group which is later converted to the amino group by reduction.

When the compound resulting after N-acylation contains a sulphoxide group at the 1-position, this may be reduced by conventional methods, e.g. with triphenylphosphine and acetyl chloride. In the above process, the acylation reaction may cause a double bond shift to position 2 of the cephem nucleus, thereby producing a mixture of 2-cephem and 3-cephem isomers. If this happens, the 2-cephem/3-cephem mixture can be converted to the 3-cephem isomer by oxidation of the mixture to the sulphoxide followed by reduction. This is, of course, a standard method for the preparation of 3-cephems from 2-cephems, and is described for example in British Pat. No. 1,280,693. One such method is again treatment with triphenylphosphine and acetyl chloride.

Compounds of formula (I) may also be prepared by reaction of a compound of formula (IX):

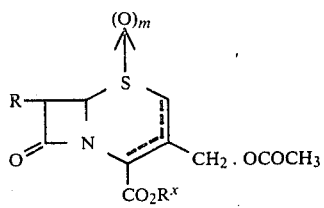

wherein $R^x$ is hydrogen or a carboxyl blocking group, m is zero or 1, the dotted line represents a bond in the 2- or 3-position and R is as defined in formula (I) and wherein any reactive groups, (such as amine carboxy and hydroxy groups) may be blocked; with a thiol of formula (IXA):

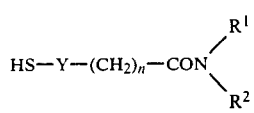

wherein Y, n, $R^1$ and $R^2$ are as defined with respect to formula (I), and thereafter carrying out one of more of the following steps:

(i) converting a Δ2 isomer into the desired Δ3 isomer;
(ii) removing any N-protecting groups;
(iii) reducing a sulphoxide compound to form the desired sulphide compound;
(iv) removal of any blocking groups from the group $R^x$ or the acyl side chain;
(v) converting the product to a salt or ester thereof.

Methods for isomerisation from Δ2 to Δ3 and reduction of sulphoxide are as described earlier. The remarks made about N-protecting and amine protecting groups and their removal also apply in this case.

A third method of preparation of the compounds of formula (I) in which R represents an acylamino group comprises:

(a) reacting a protected cephem of formula (X):

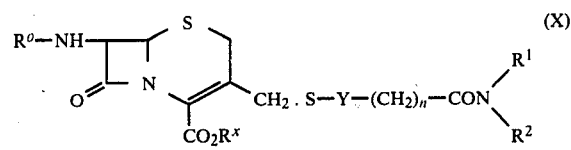

wherein $R^o$ is an acylamino group and $R^x$, Y, n, $R^1$ and $R^2$ are as defined above, to form an imino bond on the 7-amino atom;

(b) reacting the resulting compound to introduce a group $QR_f$ on the imino carbon atom, wherein Q is oxygen, sulfur or nitrogen and $R_f$ is an alkyl group of from 1 to 12 carbon atoms or an aralkyl group of from 5 to 14 carbon atoms, to form an iminoether, iminothioether or amidine (when Q is O, S or N respectively);

(c) reacting with an acylating derivative of an acid of formula (VII) above;

(d) treating with water or an alcohol; and (e) thereafter if necessary carrying out one or more of the steps (i)–(v) above.

A fourth method of preparation of compounds of formula (I) wherein R is an acylamino group comprises:

(a) reacting a compound of formula (X):

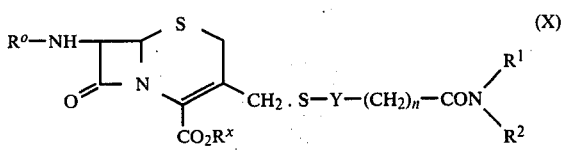

in which $R^x$ is hydrogen or a carboxyl blocking group, $R^o$ is an acyl radical and Y, n, $R^1$ and $R^2$ are as defined with respect to formula (I), with an acylating agent that provides an acyl group $R^q$, in which reactive groups may be blocked, in the presence of a trihydrocarbyl silyl derivative of a sulphonamide or of succinamide, phthalimide, cyanoacetamide, trifluoroacetamide, benzamide, p-nitrobenzamide, or trichloroacetamide to produce a compound of general formula (XII):

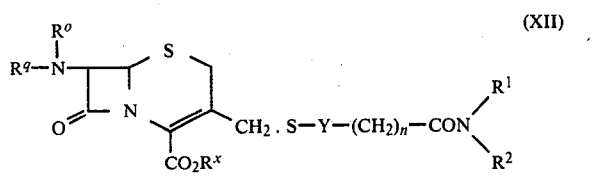

(b) replacing the $R^o$ group in the product by hydrogen to produce a compound of formula (I) in which the —CO₂H and R may be protected by blocking groups, followed if necessary by removing any such blocking groups.

Reagents and conditions for such a process are described in British Patent specification No. 1,348,986.

The compounds of formula (I) wherein the group R is of formula (XIII):

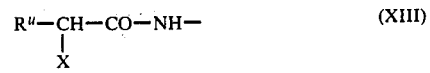

in which X is acylureido may be prepared by reaction of a compound of formula (XIV) or an N-protected derivative thereof:

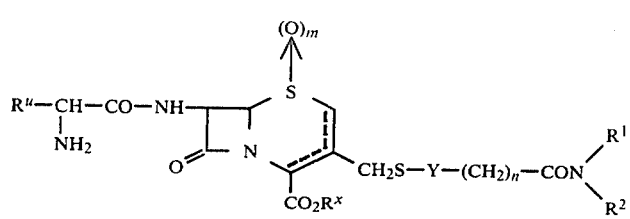

(XIV)

wherein $R^u$ is as defined with respect to formula (i) above, $R^x$ is hydrogen or a carboxyl blocking group, m is zero or 1, the dotted line represents a bond in the 2- or 3- position, and Y, n, $R^1$ and $R^2$ are as defined with respect to formula (I), with an N-acylating derivative of an acid of formula (XV):

(XV)

wherein $R^y$, and Z are as defined above, and thereafter, if necessary carrying out one or more of the steps (i)–(v) above.

The compounds of formula (I) wherein the group R is of formula (XIII) in which X represents a carboxy group may be prepared by the alkaline hydrolysis of a compound of formula (I) wherein R is of formula (XIII) in which X is an esterified carboxy group.

The hydrolysis is preferably carried out in aqueous medium in the presence of a mild base, such as for example, alkali metal bicarbonates, carbonates, or borate. A preferred base is sodium borate. If the compound in which X is an esterified carboxy group additionally has an esterified carboxy group at position 4 of the cephem nucleus, then this diester is unlikely to be soluble in water and a suitable solvent must be chosen to dissolve the ester. In such a case the choice of basic reagent to effect the hydrolysis would depend on the solvent employed.

The compounds of formula (I) wherein the group R is of formula (XVI):

(XVI)

wherein $R^u$ is as defined with respect to formula (i) above and $R^{10}$ is an ester group may be prepared by esterification of a compound of formula (XVII) or a reactive esterifying derivative thereof:

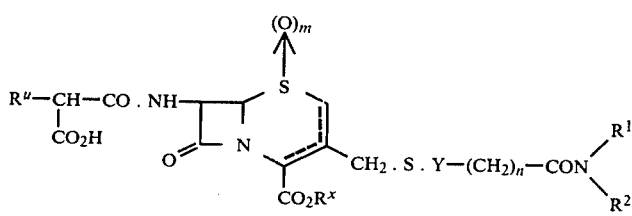

(XVII)

wherein $R^x$ is hydrogen or a carboxyl blocking group, m is zero or 1, the dotted line represents a bond in the 2- or 3- position, and Y, n, $R^1$ and $R^2$ are as defined with respect to formula (I), with an esterifying derivative of an acid of formula $R^{10}$ OH, and thereafter if necessary carrying out one or more of the steps (i)–(v) above.

Many methods of esterification using several different combinations of reactive esterifying derivatives are known from the literature. For example, the esterification reaction defined above may be achieved by reacting compound (XVII) or a salt thereof with the acid $R^{10}$ OH or an alkylsulphonate, or arylsulphonate thereof or a halide $R^{10}$-Hal, (wherein Hal represents a halogen atom). Alternatively a mixed anhydride of the compound (XVII) may be reacted with the acid $R^{10}$ OH. The mixed anhydride may be formed with any aliphatic or aromatic acyl group derived from a second carboxylic acid, but generally alkoxy carbonyl groups (e.g. $C_2H_5O.CO$) are satisfactory.

Usually it will be found satisfactory to react the sodium or potassium salt of compound (XVII) with a halide $R^{10}$-Hal, especially where Hal represents bromine or chlorine.

Another reactive esterifying derivative of compound (XVII) above is the acid halide, particularly the acid chloride. This compound may be reacted with the acid $R^{10}$OH in the presence of an acid binding agent to prepare the desired ester of this invention.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The compositions may be formulated for administration by any route, such as oral, topical or parenteral. The compositions may be in the form of tablets, capsules, powders, granules, lozenges, creams of liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrolidone fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous of oily suspensions, solutions, emulsions, syrups, or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired convent on flavouring or colouring agents.

Suppositories will contain conventional suppository bases, e.g. cocoa, butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, agents such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg. of the active ingredient. The dosage as employed for adult human treatment will preferably range from 100 to 3000 mg. per day, for instance 1500 mg. per day, depending on the route and frequency of administration.

The cephalosporin of formula (I) may be the sole therapeutic agent in the compositions of the invention or a combination with other antibiotics may be employed. Advantageously the compositions also comprise a compound of formula (XVIII) or a pharmaceutically acceptable salt or ester thereof:

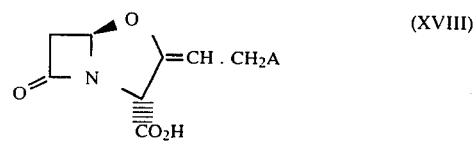
(XVIII)

wherein A is hydrogen or hydroxyl.

Preferably the compound of formula (XVIII) is clavulanic acid of formula (XIX) or a pharmaceutically acceptable salt or ester thereof:

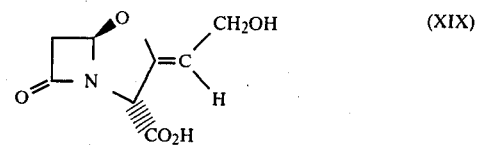
(XIX)

The preparation of these compounds is described in Belgium Patent Nos. 827,926, 836,652 and West German Offenlegungsschrift No. 2,616,088.

It will be clear that the side-chain of the cephalosporins of formula (I) contains a potentially asymmetric carbon atom. This invention includes all the possible epimers of compounds (I) as well as mixtures of them.

The following Examples illustrate the preparation of some of the compounds of this invention.

EXAMPLE 1

(a) 5-Mercapto-1,3,4-oxadiazol-2-ylacetamide

Crude ethyl 5-mercapto-1,3,4-oxadiazol-5-ylacetate (25 g) in ethanol (150 ml) was saturated with ammonia gas and stirred at room temperature for 70 hours. The solvent was removed in vacuo, the residue dissolved in water, acidified and extracted with ethyl acetate. The extracts were washed with water and saturated brine, dried and evaporated to give a brown gum. This was extracted with boiling 50% ethyl acetate in light petroleum bp 60°–80° C. to leave a yellow solid which was heated in ethyl acetate, allowed to cool and the insoluble product collected, 2.41 g (12.7%) m.p. 160°–163° C.; $\nu$max (nujol) 1675 cm$^{-1}$; $\delta[(CD_3)_2SO]$, 3.68 (2H, s, —CH$_2$—), 7.52 (2H, d, J=26 Hz, —CONH$_2$), 14.40 (1H, bs, —SH). Found: C, 30.66: H, 3.21; N, 25.50; S, 20.28. $C_4H_5N_3O_2S$ requires C, 30.19; H, 3.14; N, 26.42; S, 20.13%.

(b) 7-(Thien-2-ylacetamido)-3-(2-carbamoylmethyl-1,3,4-oxadiazol-5-ylthio)methylceph-3-em-4-carboxylic acid Sodium cephalothin (2.09 g, 5.0 mmole), 5-mercapto-1,3,4-oxadiazol-2-ylacetamide (0.84 g., 5.5 mmole) and sodium bicarbonate (0.42 g., 5.0 mmole) in pH 6.5 phosphate buffer (25 ml) were heated at 60° C. for 6.5 hours, then poured onto crushed ice (~25 g), washed with ethyl acetate (2×20 ml), acidified to pH 2.0 with N hydrochloric acid and extracted with ethyl acetate (3×50 ml). The extracts were washed with water (2×20 ml) and saturated brine (20 ml), dried and evaporated to dryness in vacuo to give a gummy solid. This was extracted with hot ethyl acetate (10 ml) to leave the product as an off white solid, 1.23 g., 49.8%; t.l.c. (SiO$_2$; n-butanol, acetic acid, water; 12:3:5) Rf=0.41; $\lambda$max (95% ethanol), 272 nm ($\epsilon$m=9,650); $\delta[(CD_3)_2SO]$, 3.5–4.0 (2H,m, C$_2$ methylene), 3.85 and 3.90 (4H, 2×s, 2×—CH$_2$CO—), 4.33 and 4.49 (2H, AB quartet, J=14 Hz, —CH$_2$S—), 5.22 (1H,d, J=5 Hz, C$_6$ proton), 5.81 (1H,dd, J=5,8 Hz, C$_7$ proton), 7.0–7.6 (3 H,m, thienyl protons), 7.65 (2H, d, J=26 Hz, —CONH$_2$), 9.33 (1H,d, J=8 Hz, —CONH—).

EXAMPLE 2

(a) 5-Mercapto-1,3,4-oxadiazol-2-ylcarboxamide

Crude ethyl 5-mercapto-1,3,4-oxadiazol-5-ylcarboxylate (45 g) in ethanol (200 ml) was saturated with ammonia gas and then stirred at room temperature for 3 days. The precipitate was collected, washed with ethanol and air dried to yield a cream solid, 40.65 g. The solid was dissolved in water (150 ml), the solution filtered, then acidified and the precipitated product collected, washed with water and dried in vacuo, 26.12 g, (69.4%), m.p. 208°–210° C.; $\nu$max (nujol) 1680 cm$^{-1}$; $\delta[(CD_3)_2SO]$, 8.47 (2H,d, J=17 Hz, —CONH$_2$), 13.75 (1H,bs, —SH). Found: C, 24.46; H, 2.12; N, 28.57; S, 21.51. C$_3$H$_3$N$_3$O$_2$S requires: C, 24.83; H, 2.08; N, 28.95; S, 22.09%.

(b) 7-(Thien-2-ylacetamido)-3-(2-carbamoyl-1,3,4-oxadiazol-5-ylthio)methylceph-3-em-4-carboxylic acid Sodium cephalothin and 5-mercapto-1,3,4-oxadiazol-2-yl-carboxamide were reacted together as described in example 1b. The dried ethyl acetate extracts were evaporated to dryness in vacuo and the residue triturated with anhydrous ether to give the cephalosporin free acid (1.85 g). This was dissolved in acetone (20 ml), treated with 2 N sodium 2-ethylhexanoate in methyl isobutyl ketone (1.85 ml) and the precipitated sodium salt collected, washed with acetone and ether and dried 1.48 g (58.9%); t.l.c. (SiO$_2$; B.S.W.; 12:3:5) Rf=0.45; $\lambda$max (95% ethanol) 272 nm ($\epsilon$m=11,200); $\delta[(CD_3)_2SO+D_2O]$, 3.3–3.9 (2H,m, C$_2$ methylene), 3.87 (2H,s, —CH$_2$CO—), 4.3–4.7 (2H,m, —CH$_2$S—), 5.07 (1H,d, J=5 Hz, C$_6$ proton), 5.4–5.9 (1H,m, C$_7$ proton), 6.9–7.7 (3H,m, thienyl protons).

EXAMPLE 3

(a) 5-Mercapto-1H-tetrazol-1-ylacetamide

Ethyl 5-mercapto-1H-tetrazol-5-ylacetate (15.0 g) was dissolved in ethanol (50 ml), the solution was saturated with ammonia gas then set aside for 36 hours. The precipitated mass was collected, washed with ethanol (20 ml), dried and dissolved in water (100 ml). The solution was treated with decolourising charcoal, filtered, acidified with concentrated hydrochloric acid and cooled in an ice bath. The product crystallised as needles and was collected, washed with a little water and dried in vacuo, 9.51 g., (75.0%) m.p. 214°–216° C. (d), $\nu$max (nujol) 1695 cm$^{-1}$; $\delta[(CD_3)_2SO]$, 7.72 (2H,d, J=22 Hz, —NH$_2$), 5.02 (2H,s, —CH$_2$—). Found: C, 22.39; H, 2.18; N, 43.82; S, 20.16. C$_3$H$_5$N$_5$OS requires: C, 22.64; H, 3.17; N, 44.00; S, 20.14%.

(b) 7-(Thien-2-ylacetamido)-3-(1-carbamoylmethyl-1H-tetrazol-5-ylthio)methylceph-3-em-4-carboxylic acid Sodium cephalothin and 5-mercapto-1H-tetrazol-1-ylacetamide were reacted together as described in example 1b. The dried ethyl acetate extracts were concentrated to ~15 ml, diluted with anhydrous ether (15 ml) and the precipitated free acid collected, washed with ether and dried (1.26 g). This was dissolved in acetone and treated with 2 N sodium 2-ethylhexanoate in methyl isobutyl ketone to give the sodium salt, 1.17 g, (45.3%); t.l.c. (SiO$_2$; B.A.W., 12:3:5) Rf=0.38; $\lambda$max (95% ethanol) 273 nm ($\epsilon$m=9,550); $\delta[(CD_3)_2SO]$, 3.3–3.8 (2H,m, C$_2$ methylene), 3.83 (2H,s, —CH$_2$CONH—), 4.1–4.7 (2H,m, —CH$_2$S—), 5.04 (1H,d, J=5 Hz, C$_6$ proton), 5.17 (2H,s, —CH$_2$CONH$_2$), 5.75 (1H, dd, J5 and 8H$_2$, C$_7$ proton) 6.9–7.6 (3H, m, thienyl protons), 7.92 (2H, d, J=40 Hz, —CONH$_2$), 9.20 (1H,d, J=9 Hz, —CONH—).

EXAMPLE 4

(a) 5-Mercapto-1,3,4-thiazdiazol-2-ylacetamide

Ethyl 5-mercapto-1,3,4-thiadiazol-2-ylacetate (8.20 g) in ethanol (25 ml) was saturated with ammonia gas and set aside for three days. The black precipitate formed was filtered off and discarded, the filtrate was evaporated to dryness, dissolved in dilute sodium bicarbonate solution, treated with decolourising charcoal, acidified and ethyl acetate (2×25 ml) extracted. The extracts were concentrated in vacuo to ~10 ml and the product crystallised out, 1.21 g, 17.2%, m.p. 173°–175°. The aqueous phase was concentrated to ~20 ml and cooled to yield more crystalline product, 0.72 g, 10.2%, m.p. 174°–176°; $\nu$max (nujol) 1655 cm$^{-1}$; $\delta[(CD_3)_2SO]$, 3.88 (2H,s, —CH$_2$CO—), 7.60 (2H,d, J 27 Hz, —CONH$_2$), 14.52 (1H,bs, —SH). Found: C, 27.24; H, 3.00; N, 24.25; S, 36.28; C$_4$H$_5$N$_3$OS$_2$ requires: C, 27.42; H, 2.88; N, 23.98; S, 36.60%

(b) 7-(Thien-2-ylacetamido)-3-(carbamoylmethyl-1,3,4-thiadiazol-5-ylthio) methylceph-3-em-4-carboxylic acid Sodium cephalothin (1.05 g, 2.5 mmole) and 5-mercapto-1,3,4-thiadiazol-2-yl-acetamide (0.48 g, 2.75 mmole) were reacted together as described in example 1b. The reaction mixture was poured onto ice, washed with ethyl acetate, covered with ethyl acetate and acidified. The product precipitated as a pale yellow solid, this was filtered off, washed with water and ethyl acetate and dried, 0.87 g, (68.1%); t.l.c. (SiO$_2$; B.A.W.; 12:3:5) Rf=0.41; $\nu$max (95% ethanol) 276 nm ($\epsilon$=12300); $\delta[(CD_3)_2SO]$ 3.85 (2H,s, C$_2$ methylene), 3.95 (2H,s, —CH$_2$CONH—), 4.19 (2H,s, —CH$_2$CONH$_2$), 4.41 and 4.67 (2H, AB quartet, J 14 Hz, —CH$_2$S—), 5.22 (1H,d, J 5 Hz, C$_6$ proton), 5.90 (1H,dd, J 5 and 8 Hz, C$_7$ proton), 6.8–8.1 (6H,m, —CO$_2$H, —CONH$_2$ and thienyl protons), 8.85 (1H,d, J 8 Hz, —CONH—).

EXAMPLE 5

7-[D-$\alpha$(3-Benzoyl-3-methylureido)phenylacetamido]-3-(2-carbamoylmethyl-1,3,4-oxadiazol-5-ylthio)methylceph-3-em-4-carboxylic acid D-$\alpha$(Benzoyl-3-methylureido)benzyl cephalosporin (1.42 g., 2.5 mmole) and 5-mercapto-1,3,4-oxadiazol-2-ylacetamide (0.42 g., 2.75 mmole) were dissolved in N-sodium bicarbonate solution (5 ml) and water (20 ml) and then heated at 60° for 6.5 hours. The solution was poured onto ice (~20 g), washed with ethyl acetate (2×20 ml), acidified and extracted with ethyl acetate (3×20 ml). The combined extracts were washed with water (2×25 ml) and saturated brine (20 ml), dried and concentrated to ~10 ml. in vacuo, diluted with anhydrous ether (10 ml) and the precipitate collected, washed with ethyl acetate (~5 ml) and dried to give a cream solid (0.88 g); t.l.c. (SiO$_2$; B.A.W; 12:3:5) Rf=0.45; $\delta[(CD_3)_2CO]$, 3.20 (3H,s, >N—CH$_3$), 3.6–4.0 (2H,m, C$_2$ methylene), 4.03 (2H,s, —CH$_2$CO—), 4.1–4.7 (2H,m, —CH$_2$S—), 5.13 (1H,d, J=5 Hz, C$_6$ proton), 5.8–6.2 (2H,m, PhCH< and C$_7$ proton), 7.0–8.2 (13H,m, 2×Ph—, —CONH$_2$ and —CO$_2$H), 8.62 (1H,d, J=9 Hz, —CONH—), 10.28 (1H,d, J=7 Hz, —CHNHCO—). The free acid (0.88 g) was dissolved in acetone (10 ml) and treated with 2 N sodium 2-ethylhexanoate in methyl isobutyl ketone (0.66 ml). The precipated sodium salt was collected, washed with acetone and ether and dried

EXAMPLE 6

7-[D-α(3-Benzoyl-3-methylureido)phenylacetamido]-3-(2-carbamoyl-1,3,4-oxadiazol-5-ylthio)methylceph-3-em-4-carboxylic acid D-α(3-Benzoyl-3-methylureido)benzyl cephalosporin (1.42 g, 2.5 mmole) was treated with 5-mercapto-1,3,4-oxadiazol-2-ylcarboxamide (0.40 g, 2.75 mmole) as described in example 5. The dried ethyl acetate extracts were evaporated to dryness and the residue triturated with anhydrous ether to give a solid (1.15 g); t.l.c. (SiO$_2$; B.A.W.; 12:3:5) Rf=0.43; δ[(CD$_3$)$_2$CO], 3.20 (3H,s, >NCH$_3$), 3.77 (2H,bs, C$_2$ methylene), 4.47 (2H,bs, —CH$_2$S—), 5.12 (1H,d, J=5 Hz, C$_6$ proton), 5.7–6.2 (2H,m, PhC$\underline{H}$< and C$_7$ proton), 6.6–8.2 (1.3H,m, —CO$_2$H, —CONH$_2$ and aromatic protons), 8.57 (1H,d, J=9 Hz, —CONH—), 10.27 (1H,d, J=8 Hz, —CHN$\underline{H}$CO—). This free acid was dissolved in acetone and treated with 2 N sodium 2-ethylhexanoate in methyl isobutyl ketone (0.85 ml) to precipitate the sodium salt, 0.83 g, (49.4%), λmax (95% ethanol) 267 nm (εm=14220).

EXAMPLE 7

7-[D-α-(3-Benzoyl-3-methylureido)phenylacetamido]-3-(1-carbamoylmethyl-1H-tetrazol-5-ylthio)methylceph-3-em-4-carboxylic acid Prepared from D-α(3-benzoyl-3-methylureido)benzylcephalosporin (1.42 g; 2.5 mmole) and 5-mercapto-1H-tetrazol-1-ylacetamide (0.44 g, 2.75 mmole) as in example 5 to give the free acid (0.95 g); t.l.c. (SiO$_2$; B.A.W; 12:3:5) Rf 0.37; δ[(CD$_3$)$_2$CO] 3.21 (3H,s, >NCH$_3$), 3.76 (2H,bs, C$_2$ methylene), 4.46 (2H,bs, —CH$_2$S—), 5.10 (1H,d, J=5 Hz, C$_6$ proton), 5.28 (2H,s, —C$\underline{H}_2$CONH$_2$), 5.7–6.2 (2H,m, PhC$\underline{H}$< and C$_7$ proton), 6.3–7.8 (13H,m, —CO$_2$H, —CONH$_2$ and aromatic protons), 8.63 (1H,d, J=8 Hz, —CONH—), 10.29 (1H,d, J=7 Hz, —CHN$\underline{H}$CO—). The free acid in acetone was treated with 2 N sodium 2-ethylhexanoate to give the sodium salt; 0.98 g, (58.8%); λmax (95% ethanol) 264 nm (ε 10,820).

EXAMPLE 8

(a)

7-[D-α-(t-Butoxycarbonylamino)phenylacetamido]-3-(1-carbamoylmethyl-1,3,4-oxadiazol-5-ylthio)methylceph-3-em-4-carboxylic acid N-t-Butoxycarbonyl cephaloglycin (1.52 g., 3.0 mmole), 5-mercapto-1,3,4-oxadiazol-2-ylacetamide (0.48 g., 3.0 mmole) and sodium bicarbonate (0.50 g., 6.0 mmole) in pH 6.5 phosphate buffer (20 ml) were heated at 70° for 3.5 hours. The solution was poured onto ice (20 g), washed with ethyl acetate (2×25 ml), acidified and extracted with ethyl acetate (3×20 ml). The combined extracts were washed with water (2×25 ml) and saturated brine (20 ml), dried, evaporated to dryness in vacuo and the residue triturated with anhydrous ether to give the product (0.93 g, 51.4%) as a cream solid; t.l.c. (SiO$_2$; B.A.W.; 12:3:5) Rf=0.36; δ[(CD$_3$)$_2$CO+D$_2$O], 1.45 (9H,s, —C(CH$_3$)$_3$), 3.72 (2H,bs, C$_2$ methylene), 4.00 (2H,s, —C$\underline{H}_2$CONH$_2$), 4.37 (2H,bs, —CH$_2$S—), 5.10 (1H,d, J=5 Hz, C$_6$ proton), 5.50 (1H,s, PhC$\underline{H}$<), 5.6–6.1 (1H,m, C$_7$ proton), 7.2–7.8 (5H, m, Ph—).

(b)

7-(D-α-Aminophenylacetamido)-3-(2-carbamoylmethyl-1,3,4-oxadiazol-5-ylthio)methylceph-3-em-4-carboxylic acid The t-butoxycarbonyl protected compound (0.93 g.) was suspended in anisole (2 ml) and cooled in an ice bath while cooled trifluoroacetic acid (5 ml) was added. The dark brown solution was then stirred at R.T. for 1.5 hours then added dropwise to vigorously stirred anhydrous ether (400 ml). The precipitated trifluoroacetic acid salt was collected washed with ether and dried in vacuo 0.81 g (85.0%); λmax (95% ethanol) 266 nm (ε=9540); δ[(CD$_3$)$_2$SO+D$_2$O], 3.62 (2H,bs, C$_2$ methylene), 3.89 (2H,s, —C$\underline{H}_2$CONH$_2$), 4.32 (2H,bs, —CH$_2$S—) 4.9–5.3 (2H,m, PhC$\underline{H}$<, and C$_6$ proton), 5.7–6.0 (1H,m, C$_7$ proton), 7.57 (5H,s, Ph—).

EXAMPLE 9

(a)

7-[D-α-(t-Butoxycarbonylamino)phenylacetamido]-3-(2-carbamoyl-1,3,4-oxadiazol-5-ylthio)methylceph-3-em-4-carboxylic acid N-t-Butoxycarbonyl cephaloglycin was treated with 5-mercapto-1,3,4-oxadiazol-2-ylcarboxamide as described in example 8a to give a 33.8% yield of product; t.l.c. Rf=0.54; δ[(CD$_3$)$_2$CO], 1.45 (9H,s, —C(CH$_3$)$_3$), 3.76 (2H,bs, C$_2$ methylene), 4.46 (2H,bs, —CH$_2$S—), 5.12 (1H,d, J=5 Hz, C$_6$ proton), 5.4–5.6 (1H,m, PhC$\underline{H}$<), 5.8–6.1 (1H,m, C$_7$ proton), 6.4–8.1 (10H,m, —CO$_2$H, —CONH$_2$, —CONH—, Ph—), 8.40 (1H,d, J=8 Hz, —CONH—).

(b)

7-(D-α-Aminophenylacetamido)-3-(2-carbamoyl-1,3,4-oxadiazol-5-ylthio)methylceph-3-em-4-carboxylic acid The t-butoxycarbonyl protecting group was removed with trifluoro acetic acid in the presence of anisole to give as in example 8 (b) the trifluoro acetic acid salt of the title compound, 88.2% yield; λmax (95% ethanol) 270 nm (εm=10500); δ[(CD$_3$)$_2$SO+D$_2$)], 3.4–3.8 (2H,m, C$_2$ methylene), 4.36 (2H,bs, —CH$_2$S—), 4.9–5.3 (2H,m, PhC$\underline{H}$< and C$_6$ proton), 5.88 (1H,d, J=5 Hz, C$_7$ proton), 7.60 (5H,s, Ph—).

EXAMPLE 10

(a)

7-[D-α-(t-Butoxycarbonylamino)phenylacetamido]-3-(1-carbamoylmethyl-1H-tetrazol-5-ylthio)methylceph-3-em-4-carboxylic acid 5-Mercapto-1H-tetrazol-1-ylacetamide and N-t-butoxycarbonylcephaloglycin were reacted together as described in example 8 (a) to give the title compound 50.7%; t.l.c. Rf=0.48; δ[(CD$_3$)$_2$CO], 1.44 (9H,s, —C(CH$_3$)$_3$), 3.75 (2H,bs, C$_2$ methylene), 4.3–4.6 (2H,m, —CH$_2$S—), 5.08 (1H,d, J=5 Hz, C$_6$ proton), 5.25 (2H,s, —C$\underline{H}_2$CONH$_2$), 5.4–5.7 (1H,m, PhC$\underline{H}$<), 5.93 (1H,dd, J 5, 9 Hz, C$_7$ proton), 6.5–7.8 (9H,m, —CO$_2$H, —CHN$\underline{H}$CO—, —CONH$_2$ and Ph—), 8.44 (1H,d, J=9 Hz, —CONH—).

(b)

7-(D-α-Aminophenylacetamido)-3-(1-carbamoylmethyl-1H-tetrazol-5-ylthio)methylceph-3-em-4-carboxylic acid Treatment of the material above with trifluoroacetic acid and anisole as in example 8 (b) gave the salt of the product, 94.7% yield; λmax (95% ethanol) 270 nm (ε 6090); δ[(CD$_3$)$_2$SO+D$_2$O), 3.65 (2H,bs, C$_2$ methylene), 4.35 (2H,bs, —CH$_2$S—), 5.0-5.3 (4H,m, —CH$_2$CONH$_2$, PhCH< and C$_6$ proton), 5.87 (1H,d, J=5 Hz, C$_7$ proton), 7.57 (5H,s, Ph—).

EXAMPLE 11

7-Amino-3-(1-carbamoylmethyl-1H-tetrazol-5-ylthio)-methylceph-3-em-4-carboxylic acid 7-Aminocephalosporanic acid (5.44 g., 20 mmole) and 5-Mercapto-1H-tetrazol-1-ylacetamide (3.50 g., 2.2 mmole) were suspended in 50% aqueous acetone (200 ml) and solid sodium bicarbonate added until a clear solution was obtained, ~pH 7.0. The solution was heated at 60° for 6 hours, uncovered for the final hour which allowed most of the acetone to evaporate, then acidified to pH 4.0 and stirred in an ice bath for one hour. The solid product was collected, washed with a little cold water and dried in vacuo, 3.22 g (43.4%), δ(CF$_3$CO$_2$H) 4.00 (2H,bs, C$_2$ methylene), 4.69 (2H,bs, —CH$_2$S—), 5.56 (4H,s, —CH$_2$CO$_2$NH$_2$ and β-lactam protons), 7.4-7.8 (2H,m, —CONH$_2$).

EXAMPLE 12

(a) N-Methyl-5-Mercapto-1H-tetrazol-1-ylacetamide

Ethyl 5-mercapto-1H-tetrazol-1-ylacetate (2.0 g) was dissolved in 33% methylamine in ethanol (20 ml) and stood overnight at R.T. The solution was evaporated to dryness in vacuo, the residue dissolved in water (20 ml), adicified and ether extracted (6×50 ml). The extracts were dried and evaporated to give a crystalline solid which was crystallised from ethyl acetate, 0.59 g (32.0%) m.p. 167°-168°; δ[(CD$_3$)$_2$CO] 2.88 (3H,d, J 5 Hz, —NHCH$_3$), 5.15 (2H,s, —CH$_2$CO—), 6.70 (1H,m, —NH—), 12.9 (1H,bs, —SH). Found: C, 27.53; H, 4.17; N, 40.07; S, 18138. C$_4$H$_7$N$_5$OS requires: C, 27.74; H, 4.07; N, 40.44; S, 18.51%.

(b) 7-(Thien-2-ylacetamido)-3-[1-(N-methylcarbamoylmethyl)-1H-tetrazol-5-ylthio]methylceph-3-em-4-carboxylic acid Sodium cephalothin (1.05 g, 2.5 mmole), N-methyl-5-mercapto-1H-tetrazol-1-ylacetamide (0.48 g, 2.75 mmole) and sodium bicarbonate (0.21 g, 2.5 mmole) in pH 6.5 phosphate buffer (15 ml) were heated at 60° for 6.5 hours, poured onto ice, washed with ethyl acetate (2×20 ml), acidified and extracted with ethyl acetate (3×20 ml). The extracts were washed with water (2×35 ml) and saturated brine (20 ml), dried, evaporated to dryness in vacuo and the residue triturated with ether to give a cream coloured solid, 0.84 g. This was dissolved in acetone (50 ml), treated with 2 N sodium 2-ethylhexoate in 4-methyl-pentan-2-one (0.83 ml), diluted with anhydrous ether (200 ml) and the precipitated sodium salt collected, washed with ether and dried in vacuo, 0.76 g (57.3%); t.l.c. (SiO$_2$; n-butanol, acetic acid, water; 12:3:5) Rf=0.43; λmax (95% ethanol) 272 nm (ε 9,700) ε (free acid) [(CD$_3$)$_2$CO] 2.82 (3H,d, J 5 Hz, —NHCH$_3$), 3.83 (2H,s, C$_2$ methylene), 3.98 (2H,s, —CH$_2$CO—), 4.40 and 4.53 (2H, AB quartet, J 15 Hz, —CH$_2$S—), 5.12 (1H,d, J 5 Hz, C$_6$ proton) 5.23 (2H,s, —CH$_2$CONHCH$_3$), 5.90 (1H,dd, J 5 and 8 Hz, C$_7$ proton), 7.0-7.6 (3H,m, thienyl protons), 7.8 (1H,m, —CONH—), 8.52 (1H,d, J 8 Hz, —CONH—).

EXAMPLE 13

(a) N,N-Dimethyl-5-mercapto-1H-tetrazol-1-ylacetamide

Ethyl 5-mercapto-1H-tetrazol-1-ylacetate (1.5 g) in ethanol (10 ml) and 33% dimethylamine in ethanol (6 ml) were mixed and set aside for seven days. Further 33% dimethylamine in ethanol (6 ml) was added and the solution left for 7 more days then evaporated to dryness in vacuo. The residue was dissolved in water (50 ml), adjusted to pH 1.8, and concentrated to ca 20 ml in vacuo. The solution was cooled in ice and the crystalline product collected, 0.94 g (63.0%), m.p. 204°-205°; ε [(CD$_3$)$_2$CO] 3.02 and 3.28 (6H, 2×s —N(CH$_3$)$_2$), 5.35 (2H,s, —CH$_2$CO—), 7.7 (1H,bs, —SH). Found: C, 32.21; H, 5.01; N, 37.63; S, 16.99. C$_5$H$_9$N$_5$OS requires: C, 32.08; H, 4.85; N, 37.41; S, 17.13%.

(b) 7-(Thien-2-ylacetamido)-3-[1-(N,N-dimethylcarbamoylmethyl)-1H-tetrazol-5-ylthio]methylceph-3-em-4-carboxylic acid Prepared from sodium cephalothin and N,N-dimethyl-5-mercapto-1H-tetrazol-1-ylacetamide as described in example 12(b) in 44.1% yield; t.l.c. (SiO$_2$; B.A.W; 12:3:5) Rf=0.35; λmax (95% ethanol) 271 nm (ε 8,390); δ(free acid) [(CD$_3$)$_2$CO] 2.33 and 3.27 (6H, 2×s -N(CH$_3$)$_2$), 3.85 (2H,s, C$_2$ methylene), 4.00 (2H,s, —CH$_2$CO—), 4.47 (2H,bs, —CH$_2$S—), 5.20 (1H,d, J 5 Hz, C$_6$ proton), 5.55 (2H,s, —CH$_2$CON(CH$_3$)$_2$), 5.97 (1H,dd, J 5 and 9 Hz, C$_7$ proton), 6.9-8.0 (4H,m, thienyl protons and —CO$_2$H), 8.29 (1H,d, J 9 Hz, —CONH—).

EXAMPLE 14

7-[D,α-(3-Benzoyl-3-methylureido)phenylacetamido]-3-(2-carbamoyl-methyl-1,3,4-thiadiazol-5-ylthio)methylceph-3-em-4-carboxylic acid D,α-(3-Benzoyl-3-methylureido)benzyl cephalosporin (1.42 g, 2.5 mmole) and 5-mercapto-1,3,4-thiadiazol-2-ylacetamide (0.48 g, 2.75 mmole) in water (20 ml) and N sodium bicarbonate solution (5 ml) were heated at 60° for 6.5 hours, poured onto crushed ice, washed with ethyl acetate (2×25 ml), acidified and n-butanol extracted (3×20 ml). The extracts were washed with water (2×20 ml) and saturated brine (20 ml), dried, evaporated to dryness in vacuo and the residue triturated with anhydrous ether to give the free acid of the product, 1.31 g. This was dissolved in methanol (40 ml), treated with 2 N sodium 2-ethylhexoate in 4-methylpentan-2-one (0.95 ml), added to anhydrous ether (200 ml) and the precipitated sodium salt collected, washed with ether and dried in vacuo, 1.20 g (68.3%); t.l.c. (SiO$_2$; B.A.W; 12:3:5) Rf=0.46; λmax (95% ethanol) 275 nm (ε 13,700); δ[(CD$_3$)$_2$SO] 3.22 (3H,s, >N—CH$_3$), 3.5-4.0 (2H,m, C$_2$ methylene), 4.18 (2H,s, —CH$_2$CONH$_2$), 4.2-4.8 (2H,m, —CH$_2$S—), 5.12 (1H,d, J 5 Hz, C$_6$ proton), 5.8-6.1 (2H,m, PhCH< and C$_7$ proton), 7.0-8.0 (12H,m, —CONH$_2$, 2×Ph—), 9.38 (1H,d, J 9 Hz, —NH—), 10.18 (1H,d, J 8 Hz, —NH—).

EXAMPLE 15

7-[D,α-(3-2'-Chlorobenzoyl-3-methylureido)-phenylacetamido]-3-(1-carbamoylmethyl-1H-tetrazol-5-ylthio)methylceph-3-em-4-carboxylic acid D,α-(3-2'-Chlorobenzoyl-3-methylureido)benzyl cephalosporin (1.86 g, 3.0 mmole) and 5-mercapto-1H- tetrazol-1-ylacetamide (0.59, 3.7 mmole) in water (30 ml) were adjusted to pH 5.4 with N sodium bicarbonate solution then stirred at 70° for 3 hours, adjusted to pH 7.0, poured onto crushed ice (ca 20 g), washed with ethyl acetate (2×40 ml), acidified and extracted with ethyl acetate (3×40 ml). The extracts were washed with water (2×40 ml), dried, evaporated to dryness in vacuo and the residue triturated with ether to give the free acid, 1.0 g; t.l.c. (SiO$_2$; B.A.W; 12:3:5) Rf=0.35. This was dissolved in acetone (10 ml), treated with 2 N sodium 2-ethylhexoate in 4-methylpentan-2-one (0.71 ml) and the precipitated sodium salt collected, washed with acetone and ether and dried, 0.90 g (41.6%); λmax (95% ethanol) 270 nm (ε9,000), δ[(CD$_3$)$_2$SO] 2.95 (3H,s, >NCH$_3$), 3.3–3.5 (2H,m, C$_2$ methylene), 4.2–4.4 (2H,m, —CH$_2$S—), 4.92 (1H,d, J 5 Hz, C$_6$ proton), 5.07 (2H,s, —CH$_2$CONH$_2$), 5.5–5.8 (2H,m, PhCH< and C$_7$ proton), 7.2–8.1 (1H,m, —CONH$_2$ and aromatic protons), 9.3–9.5 (1H,m, —NH—), 9.8–10.0 (1H,m, —NH—).

EXAMPLE 16

7-[D-α-(3-2'-Furoyl-3-methylureido)phenylacetamido]-3-(1-carbamoyl-methyl-1H-tetrazol-5-ylthio)methylceph-3-em-4-carboxylic acid D,α-(3-2'-Furoyl-3-methylureido)benzyl cephalosporin and 5-mercapto-1H-tetrazol-1-ylacetamide were reacted together as described in example 15 to give the sodium salt, 25.6%; λmax (95% ethanol) 269 nm (ε 23,200); δ[(CD$_3$)$_2$SO] 3.32 (3H,s, >N—CH$_3$), 3.2–3.4 (2H,m, C$_2$ methylene), 4.2–4.4 (2H,m, —CH$_2$S—), 4.89 (1H,d, J 5 Hz, C$_6$ proton), 5.06 (2H,s, —CH$_2$CONH$_2$), 5.5–5.8 (2H,m, PhCH< and C$_7$ proton), 6.6–6.8 (1H,m, furoyl proton), 7.3–7.6 (8H,m, —CONH$_2$, furoyl and aromatic protons), 7.97 (1H,m, furoyl proton), 9.2–9.5 (1H,m, —NH—), 9.6–9.8 (1H,m, —NH—).

EXAMPLE 17

7-[D-α-(3-isoButyryl-3-methylureido)-phenylacetamido]-3-(1-carbamoyl-methyl-1H-tetrazol-5-ylthio)methylceph-3-em-4-carboxylic acid 7-(D,α-Aminophenylacetamido)-3-(1-carbamoyl-methyl-1H-tetrazol-5-ylthio)methylceph-3-em-4-carboxylic acid trifluoroacetic acid salt (3.09 g, 5.0 mmole) in water (25 ml) and THF (10 ml) was adjusted to pH 7.0 with 2.5 N sodium hydroxide solution then treated with N-chlorocarbonyl-N-methylisobutyramide (prepared from N-methylisobutyramide, 10 mmole) in THF (10 ml) while pH 6.5 was maintained by simultaneous addition of 2.5 N sodium hydroxide solution. The mixture was diluted with water (100 ml), ethyl acetate washed (2×30 ml), acidified and ethyl acetate extracted (3×20 ml). The extracts were washed with water (3×25 ml), dried, treated with 2 N sodium 2-ethylhexoate in 4-methylpentan-2-one, diluted with ether and the precipitated sodium salt collected, washed with ether and dried in vacuo, 0.80 g (27.0%); t.l.c. (SiO$_2$; n-butanol, ethanol, water; 2:2:1) Rf=0.43; λmax (KBr) 1760 cm$^{-1}$; λmax (95% ethanol) 270 nm (ε 7,900); δ[(CD$_3$)$_2$SO] 1.06 (6H,d, J 7 Hz, (CH$_3$)$_2$CH—), 3.05 (1H,m, (CH$_3$)$_2$CH—), 3.18 (3H,s, >NCH$_3$), 3.45 (2H,m, C$_2$ methylene), 4.24 (2H,m, —CH$_2$S—), 4.90 (1H,d, J 5 Hz, C$_6$ proton), 5.01 (2H,s, —CH$_2$CONH$_2$), 5.4–5.7 (2H,m, PhCH< and C$_7$ proton), 7.0–8.0 (7H,m, —CONH$_2$ and aromatic protons), 9.33 and 10.05 (2H, 2xd, 2×—NH—).

EXAMPLE 18

7-[D-α-(3-Methyl-3-3'-thienoylureido)-phenylacetamido]-3-(1-carbamoyl-methyl-1H-tetrazol-5-ylthio)methylceph-3-em-4-carboxylic acid 7-(D-α-Aminophenylacetamido)-3-(1-carbamoyl-methyl-1H-tetrazol-5-ylthio)methylceph-3-em-4-carboxylic acid T.F.A. salt was acylated with N-chlorocarbonyl-N-methyl-3-thenoamide as described in example 17 to give the required sodium salt, 30.3% yield; λmax (95% ethanol) 240 nm (ε 15,800), 270 nm (ε 10,400); δ[(CD$_3$)$_2$SO] 3.17 (3H,s, >NCH$_3$), 3.1–3.7 (2H,m, C$_2$ methylene), 4.2–4.4 (2H,m, —CH$_2$S), 4.87 (1H,d, J 5 Hz, C$_6$ proton), 5.06 (2H,s, —CH$_2$CONH$_2$), 5.5–5.7 (2H,m, PhCH< and C$_7$ proton), 7.40 (5H,s, Ph—), 7.2–8.2 (3H,m, —CONH$_2$ and thienyl protons), 9.2–9.5 (1H,m, —NH—), 9.7–10.0 (1H,m, —NH—).

EXAMPLE 19

7-[D-α-(3-3'-Furoyl-3-methylureido)phenylacetamido]-3-(1-carbamoyl-methyl-1H-tetrazol-5-ylthio)methylceph-3-em-4-carboxylic acid Acylation of 7-(D,α-aminophenylacetamido)-3-(1-carbamoylmethyl-1H-tetrazol-5-ylthio)methylceph-3-em-4-carboxylic acid with N-chlorocarbonyl-N-methyl-3-furamide as described in example 17 gave a 19.9% yield of sodium salt; λmax (95% ethanol) 270 nm (ε9,500); δ[(CD$_3$)$_2$SO] 3.32 (3H,s,>NCH$_3$), 3.2–3.7 (2H,m, C$_2$ methylene), 4.2–4.4 (2H,s, —CH$_2$S—), 4.92 (1H,d, J 5 Hz, C$_6$ proton), 5.09 (2H,s, —CH$_2$CONH$_2$), 5.4–5.8 (2H,m, PhCH and C$_7$ proton), 6.88–8.4 (10H,m, Ph—, —CONH$_2$ and furyl protons), 9.3–9.5 (1H,m, —NH—), 9.9–10.1 (1H,m, —NH—).

EXAMPLE 20

(a)

7-(D,α-t-Butoxycarbonylamino-4-hydroxy-phenylacetamido)-3-(1-carbamoylmethyl-1H-tetrazol-5-ylthio)methylceph-3-em-4-carboxylic acid D,α-t-Butoxycarbonylamino-4-hydroxybenzyl cephalosporin (2.61 g, 5 mmole), 5-mercapto-1H-tetrazol-1-ylacetamide (0.795 g, 5 mmole) and sodium bicarbonate (0.84 g, 10 mmole) in pH 6.5 phosphate buffer (25 ml) were heated at 70° for 4 hours, poured onto crushed ice, ethyl acetate washed (2×25 ml), acidified and ethyl acetate extracted (3×20 ml). The extracts were washed with water (2×25 ml) and saturated brine, dried and concentrated to ca 10 ml in vacuo. The precipitated solid was collected, washed with ethyl acetate (ca 2 ml) and dried, 1.47 g (47.4%) t.l.c. (SiO; B:A:W: 12:3:5) Rf=0.45; δ[(CD$_3$)$_2$CO] 1.51 (9H,s, —C(CH$_3$)$_3$)3.78 (2H,bs, C$_2$ methylene), 4.45 (2H,bs, —CH$_2$S—), 5.15 (1H,d, J 5 Hz, C$_6$ proton), 5.27 (2H,s, —CH$_2$CONH$_2$), 5.43 (1H,d, J 9 Hz, PhCH<), 5.92 (1H,dd, J 5 and 9 Hz, C$_7$ proton), 6.5–9.0 (10H,m, —OH, 2×—NH—, CO$_2$H, -CONH$_2$ and aromatic protons).

(b)

7-(D,α-Amino-4-hydroxyphenylacetamido)-3-(1-carbamoylmethyl-1H-tetrazol-5-ylthio)methylceph-3-em-4-carboxylic acid 7-(D,α-t-Butoxycarbonylamino-4-hydroxy-phenylacetamido)-3-(1-carbamoylmethyl-1H-tetrazol-5-ylthio)methylceph-3-em-4-carboxylic acid (1.40 g) was suspended in anisole (2 ml), cooled in an ice bath and treated with cooled trifluoroacetic acid (5 ml). The solution was stirred at R.T. for one hour then added dropwise to stirred anhydrous ether (350 ml). The precipitated trifluoroacetic acid salt was collected, washed with ether and dried in vacuo, 1.20 g (83.8%); λmax (95% ethanol) 275 nm (ε8,100); δ[(CD$_3$)$_2$SO] 3.4–3.9 (2H,m, C$_2$ methylene), 4.1–4.7 (2H,m, —CH$_2$S—), 4.90–5.4 (4H,m, —CH$_2$CONH$_2$,>CHCO— and C$_6$ proton), 5.7–6.1 (1H,m, C$_7$ proton), 6.5–9.0 (11H,m, —N$^+$H$_3$, —CO$_2$H, —CONH$_2$, —OH and aromatic protons), 9.5–9.8 (1H,m, —CONH—).

EXAMPLE 21

(a)

7-(D,α-t-Butoxycarbonylamino-4-hydroxy-phenylacetamido)-3-(2-carbamoylmethyl-1,3,4-thiadiazol-5-ylthio)methylceph-3-em-4-carboxylic acid D,α-t-Butoxycarbonylamino-4-hydroxybenzyl cephalosporin and 5-mercapto-1,3,4-thiadiazol-2-ylacetamide were reacted together as described in example 20(a) to give a 40.2% yield or product; t.l.c. (SiO$_2$; B.A.W.; 12:3:5) Rf=0.43; δ[(CD$_3$)$_2$CO] 1.42 (9H,s, —C(CH$_3$)$_3$), 3.75 (2H,m, C$_2$ methylene), 4.20 (2H,s, -CH$_2$CONH$_2$), 4.2–4.8 (2H,m, —CH$_2$S—), 5.12 (1H,d, J 5 Hz, C$_6$ proton), 5.43 (1H,d, J 8 Hz, >CHCO—), 5.92 (1H,dd, J 5 and 8 Hz, C$_7$ proton), 6.4–8.0 (9H,m, —OH, —CO$_2$H, —CONH$_2$, —Nh— and aromatic protons), 8.57 (1H,d, J 8 Hz, —NH—).

(b)

7-(D,α-Amino-4-hydroxyphenylacetamido)-3-(2-carbamoylmethyl-1,3,4-thiadiazol-5-ylthio)methylceph-3-em-4-carboxylic acid 7-(D,α-t-Butoxycarbonylamino-4-hydroxy-phenylacetamido)-3-(2-carbamoylmethyl-1,3,4-thiadiazol-5-ylthio)methylceph-3-em-4-carboxylic acid was treated with anisole and trifluoroacetic acid as in 20 (b) to give an 88.5% yield of product; λmax (95% ethanol) 276 nm (ε12,740); δ[(CD$_3$)$_2$SO], 3.5–3.9 (2H,m, C$_2$ methylene), 4.10 (2H,s, —CH$_2$CONH$_2$), 4.1–4.8 (2H,m, —CH$_2$S—), 4.9–5.4 (2H,m,>CHCO— and C$_7$ proton), 5.6–6.1 (1H,m, C$_7$ proton), 6.93 and 7.42 (4H, AB quartet, J 8 Hz, aromatic protons), 7.2–9.5 (7H,m, —CONH$_2$, —N$^+$H$_3$, —CO$_2$H, —OH), 9.67 (1H,d, 8 Hz, —NH—).

EXAMPLE 22

7-(2-Carboxy-2-thien-3′-ylacetamido)-3-(1-carbamoyl-methyl-1H-tetrazol-5-ylthio)methylceph-3-em-4-carboxylic acid Thien-3-ylmalonic acid (1.54 g, 8.31 mmole) and 7-amino-3-(1-carbamoylmethyl-1H-tetrazol-5-ylthio)methylceph-3-em-4-carboxylic acid (3.24 g, 8.72 mmole) in water (40 ml) were adjusted to pH 6.0 with saturated sodium bicarbonate solution, cooled in an ice bath and treated with 1-(3-dimethylaminopropyl)-3-ethylcarbodiimide hydrochloride (1.68 g, 8.72 mmole). The solution was stirred at R.T. while pH 6.0±0.1 was maintained by the addition of 5 N hydrochloric acid as required. After 2 hours sodium bicarbonate was added to pH 7.4, the solution was washed with ethyl acetate (50 ml), acidified to pH 4.0, washed with ethyl acetate (2×25 ml), acidified to pH 1.8 and n-butanol extracted (3×20 ml). The extracts were washed with water (2×20 ml) and saturated brine (20 ml), dried, evaporated to dryness and the residue triturated with anhydrous ether to give a buff coloured solid, 1.72 g. This was dissolved in methanol (25 ml), treated with 2 N sodium 2-ethylhexoate in 4-methylpentan-2-one (3.2 ml), diluted with ether (50 ml) and the precipitated sodium salt collected, washed with ether and dried in vacuo, 1.62 g (33.4%); t.l.c. (SiO$_2$; B.A.W: 12:3:5) Rf=0.24; λmax (95% ethanol) 272 nm (ε9,840), δ(D$_2$O) 3.3–4.0 (2H,m, C$_2$ methylene), 4.24 and 4.46 (2H, AB quartet, J 14.5 Hz, —CH$_2$S—), 5.25 (1H, 2×d, J 5 Hz, C$_6$ proton), 5.50 (2H,s, —CH$_2$CONH$_2$). 5.87 (1H,d, J 5 Hz, C$_7$ proton), 7.2–7.7 (3H,m, thienyl protons).

EXAMPLE 23

(a)

7-Amino-3-(2-carbamoyl-1,3,4-oxadiazol-5-ylthio)methylceph-3-em-4-carboxylic acid 7-Aminocephalosporanic acid (10.88 g, 40 mmole) and 5-mercapto-1,3,4-oxadiazol-2-ylcarboxamide (6.40 g, 44 mmole) in 50% aqueous acetone (500 ml) were treated with solid sodium bicarbonate to pH 7 then heated at 60° for 5 hours. The solution was acidified to pH 4.0 with 5 N hydrochloric acid, cooled in an ice bath for one hour and the precipitated solid collected, washed with water (100 ml) ethanol (200 ml) and ether (200 ml) and dried in vacuo, 5.87 g (41.1%), δ(CF$_3$CO$_2$H) 3.5–4.1 (2H,m, C$_2$ methylene), 4.4–4.9 (2H,m, —CH$_2$S—), 5.42 (2H,s, β-lactam protons), 7.89 (2H, d, J 28 Hz, —CONH$_2$).

(b)

7-(2-Carboxy-2-thien-3′-ylacetamido)-3-(2-carbamoyl-1,3,4-oxadiazol-5-ylthio)methylceph-3-em-4-carboxylic acid Thien-3-ylmalonic acid (0.93 g, 5 mmole) and then 7-amino-3-(2-carboamoyl-1,3,4-oxadiazol-5-ylthio)methylceph-3-em-4-carboxylic acid (1.87 g, 5 mmole) were dissolved in water (20 ml) by the addition of saturated sodium bicarbonate solution. The solution was cooled in an ice bath, adjusted to pH 6.0 with 5 N hydrochloric acid then 1-(3-dimethylaminopropyl)-3-ethyl-carbodiimide hydrochloride (1.06 g, 5.25 mmole) in water (10 ml) was added. The solution was stirred at R.T. while being maintained at pH 6.0±0.1 by the addition of 5 N hydrochloric acid as required. After 2 hours sodium bicarbonate solution was added to pH 7.5 the solution was washed with ethyl acetate (50 ml), the aqueous layer was acidified to pH 4.0, washed with ethyl acetate (2×25 ml) then covered with n-butanol (25 ml), acidified to pH 1.8 and filtered. The n-butanol layer of the filtrate was collected and the aqueous layer extracted with more n-butanol (2×25 ml). The combined extracts were washed with water (25 ml) and saturated brine (25 ml), dried, evaporated to dryness in vacuo and the residue triturated with anhydrous ether to give an off white solid (1.02 g). This was dissolved in methanol (20 ml), filtered, treated with 2 N sodium 2-ethylhexoate in 4-methylpenton-2-one (1.95 ml), diluted with anhydrous ether (100 ml) and the precipitated sodium salt collected, washed with ether and dried in vacuo, 0.90 g (32.2%); t.l.c. (SiO$_2$; B.A.W; 12:3:5) Rf=0.02; λmax (95% ethanol) 269 nm (ε=10.200), δ(D$_2$O) 3.2–3.9 (2H,m, C$_2$ methylene), 4.12 and 4.45 (2H, ABq, J 11 Hz, —CH$_2$S—), 5.0–5.3 (1H,m, C$_6$ proton), 5.95 (1H,d, J 5 Hz, C$_7$ proton), 7.2–7.7 (3H,m, thienyl protons).

EXAMPLE 24

(a)

7-Amino-3-(1-N-methylcarbamoylmethyl-1H-tetrazol-5-ylthio) methylceph-3-em-4-carboxylic acid 7-ACA and N-methyl-5-mercapto-1H-tetrazol-1-ylacetamide were reacted as in example 23a to give the title compound, 44.0% yield; $\delta(CF_3CO_2H)$, 3.05 (3H,d, J5 Hz, —CONH$\underline{CH}_3$), 3.92 (2H,s, $C_2$ methylene), 4.63 (2H,bs, —CH$_2$S—), 5.47 (4H,s, —CH$_2$CO— and $\beta$-lactam protons), 7.5–7.8 (1H,m, —CONH—).

(b)

7-(2-Carboxy-2-thien3'-ylacetamido)-3-(1,N-methylcarbamoylmethyl-1H-tetrazol-5-ylthio)methylceph-3-em-4-carboxylic acid Thien-3-ylmalonic acid and 7-amino-3-(1,N-methylcarbamoylmethyl-1H-tetrazol-5-ylthio)methylceph-3-em-4-carboxylic acid were coupled using the method described in example 23b to give the sodium salt of the title compound, 35.8% yield; t.l.c. (SiO$_2$; B.A.W; 12:3:5) Rf=0.21; $\lambda$max (95% ethanol) 271 nm ($\epsilon$=8,760); $\delta(D_2O)$, 2.67 (3H,s, —NH$\underline{CH}_3$), 3.0–3.9 (2H,m, $C_2$ methylene), 4.01 and 4.25 (2H, ABq, J 14 Hz, —CH$_2$S—), 4.9–5.1 (1H, m, $C_6$ proton), 5.13 (2H,s, —CH$_2$CO—), 5.55 (1H,d, J 5 Hz, $C_7$ proton), 6.9–7.6 (3H,m, thienyl protons).

EXAMPLE 25

(a)

7-Amino-3-(1N,N-dimethylcarbamoylmethyl-1H-tetrazol-5-ylthio)methylceph-3-em-4-carboxylic acid 7-ACA and N,N-dimethyl-5-mercapto-1H-tetrazol-1-ylacetamide were reacted as described in example 23a to give the title compound in 40.6% yield; $\delta(CF_3CO_2H)$ 3.17 and 3.32 (6H, 2×s, —CON(CH$_3$), 3.90 (2H, bs, $C_2$ methylene), 4.63 (2H,bs, —CH$_2$S—), 5.45 and 5.58 (2H, each, s and bs, —CH$_2$CO— and $\beta$-lactam protons).

(b)

7-(2-Carboxy-2-thien-3'-ylacetamido)-3-(1,N,N-dimethylcarbamoylmethyl-1H-tetrazol-5-ylthio)methylceph-3-em-4-carboxylic acid Thien-3-ylmalonic acid and 7-amino-3-(1,N,N-dimethylcarbamoylmethyl-1H-tetrazol-5-ylthio)methylceph-3-em-4-carboxylic acid were coupled using the method described in example 23b to give the sodium salt of the title compound, 30.8% yield; t.l.c. (SiO$_2$; B.A.W; 12:3:5) Rf=0.17 $\lambda$max (95% ethanol) 273 nm ($\epsilon$=9,000); $\delta(D_2O)$ 2.81 and 2.97 (6H, 2×s, —CON(CH$_3$)$_2$), 3.1–3.8 (2H,m, $C_2$ methylene), 3.9–4.4 (2H,m, —CH$_2$S—), 4.9–5.1 (1H,m, $C_6$ proton), 5.37 (2H,s, —CH$_2$CO—), 5.54 (1H,d, J5 Hz, $C_7$ proton), 6.9–7.5 (3H,m, thienyl protons).

EXAMPLE 26

(a)

7-Amino-3-(2-carbamoylmethyl-1,3,4-thiadiazol-5-ylthio) methylceph-3-em-4-carboxylic acid 7-ACA and 5-mercapto-1,3,4-thiadiazol-2-ylacetamide were reacted as described in example 23a to give the title compound in 69.8% yield; $\delta(CF_3CO_2H)$ 3.93 (2H,s, $C_2$ methylene), 4.63 (2H,s, —CH$_2$CO—), 4.82 (2H,bs, —CH$_2$S—), 5.47 (2H,s, $\beta$-lactam protons), 7.2–7.8 (2H,m, —CONH$_2$).

(b)

7-(2-Carboxy-2-thien-3'-ylacetamido)-3-(2-carbamoylmethyl-1,3,4-thiadiazol-5-ylthio)methylceph-3-em-4-carboxylic acid Thien-3-ylmalonic acid and 7-amino-3-(2-carbamoylmethyl-1,3,4-thiadiazol-5-ylthio)methylceph-3-em-4-carboxylic acid were coupled using the method described in example 23b to give the sodium salt of the title compound, 26.0% yield; t.l.c. (SiO$_2$; B.A.W; 12:3:5) Rf=0.21; $\lambda$max (95% ethanol) 276 nm ($\epsilon$=13.400); $\delta(D_2O)$ 3.1–3.7 (2H,m, $C_2$ methylene), 4.04 (2H,s, —CH$_2$CO—), 4.1–4.6 (2H,m, —CH$_2$S—), 4.8–5.0 (1H,m, $C_6$ proton), 5.4–5.6 (1H,m, $C_7$ proton), 6.9–7.5 (3H,m, thienyl protons).

EXAMPLE 27

7-[2-Carboxy-2-(4-hydroxyphenyl)acetamido]-3-(1-carbamoylmethyl-1H-tetrazol-5-ylthio)methylceph-3-em-4-carboxylic acid 4-Hydroxyphenylmalonic acid a 7-amino-3-(1-carbamoylmethyl-1H-tetrazol-5-ylthio)methylceph-3-em-4-carboxylic acid were coupled using the method described in example 23b to give the sodium salt of the title compound, 25.3% yield; t.l.c. (SiO$_2$; B.A.W; 12:3:5) Rf=0.12; $\lambda$max (95% ethanol) 273 nm ($\epsilon$=8,100); $\delta(D_2O)$ 3.1–3.7 (2H,m, $C_2$ methylene), 3.96 and 4.24 (2H, Abq, J 13 Hz, —CH$_2$S—), 4.8–5.1 (1H,m, $C_6$ proton), 5.13 (2H,s, —CH$_2$CO—), 5.50 (1H,d, 5 Hz, $C_7$ proton), 6.78 and 7.17 (4H, ABq, J 8 Hz, aromatic protons).

EXAMPLE 28

7-[2-Carboxy-2-(4-methoxyphenyl)acetamido]-3-(1-carbamoylmethyl-1H-tetrazol-5-ylthio) methylceph-3-em-4-carboxylic acid 4-Methoxyphenylmalonic acid and 7-amino-3-(1-carbamoylmethyl-1H-tetrazol-5-ylthio)methylceph-3-em-4-carboxylic acid were coupled using the method described in example 23b to give the sodium salt of the title compound, 43.2% yield; $\lambda$max (95% ethanol) 274 nm ($\epsilon$=6,630); $\delta(D_2O)$ 3.2–3.8 (2H,m, $C_2$ methylene), 3.77 (3H,s, —OCH$_3$), 4.0–4.6 (2H,m, —CH$_2$S—), 4.9–5.2 (1H,m, $C_6$ proton), 5.28 (2H,s, —CH$_2$CO—), 5.72 (1H,d, J 5 Hz, $C_7$ proton), 7.04 and 7.19 (4H, ABq, J 8 Hz, aromatic protons).

EXAMPLE 29

7-(Thien-3-ylacetamido)-3-(1-carbamoylmethyl-1H-tetrazol-5-ylthio)-methylceph-3-em-4-carboxylic acid Sodium 7-(thien-3-ylacetamido)-3-acetoxymethylceph-3-em-4-carboxylate (1.90 g, 4.6 mmole), 5-mercapto-1H-tetrazol-1-ylacetamide (0.81 g, 5.1 mmole) and sodium bicarbonate (0.42 g, 5 mmole) in pH 6.5 phosphate buffer (25 ml) were heated at 60° for 6 hours, then poured onto ice, washed with ethyl acetate (25 ml), acidified to pH 1.5 and extracted with ethyl acetate (3×20 ml). The extracts were washed with water and saturated brine, dried, evaporated to dryness and the residue triturated with anhydrous ether to give the free acid, 1.59 g. This was dissolved in acetone (25 ml), treated with 2 N sodium 2-ethylhexoate in 4-methylpentan-2-one (1.5 ml), diluted with anhydrous ether (25 ml) and the precipitated sodium salt collected, washed with ether and dried, 1.00 g, 42.1% yield; t.l.c. (SiO$_2$; B.A.W; 12:3:5) Rf=0.40; $\lambda$max (95% ethanol) 273 nm ($\epsilon$=8,200); $\delta$[(CD$_3$)$_2$SO] 3.2–3.7 (2H,m, C$_2$ methylene), 3.38 (2H,s, —CH$_2$CONH—), 4.04–4.25 (2H, ABq, J 13 Hz, —CH$_2$S—), 4.73 (1H,d, J 5 Hz, C$_6$ proton), 4.87 (2H,s, —CH$_2$CONH$_2$), 5.50 (1H,dd, J 5 and 8 Hz, C$_7$ proton), 6.9–8.2 (5H,m, thienyl protons and —CONH$_2$), 8.88 (1H,d, J 8 Hz, —CONH—).

EXAMPLE 30

(a)
7-(D,2-Formyloxy-2-phenylacetamido)-3-(1-carbamoylmethyl-1H-tetrazol-5-ylthio)methylceph-3-em-4-carboxylic acid D,2-Formyloxy-2-phenylacetyl chloride (1.07 g; 5.4 mmole) in acetone (12.5 ml) was added to a mixture of 7-amino-3-(1-carbamoylmethyl-1H-tetrazol-5-ylthio)-methylceph-3-em-4-carboxylic acid (1.86 g, 5 mmole), N sodium hydroxide (5 ml) and N sodium bicarbonate (7.5 ml) in 50% aqueous acetone (25 ml). After 2 hours the acetone was removed in vacuo, the aqueous residue was washed with ethyl acetate (2×20 ml), covered with n-butanol (15 ml) acidified to pH 1.5, filtered and the n-butanol layer of the filtrate collected. The aqueous layer was extracted with more n-butanol (2×15 ml) then the combined extracts were washed with water and saturated brine, dried, evaporated to dryness and the residue triturated with anhydrous ether to give a pale brown solid, 1.53 g. This was dissolved in methanol (20 ml) treated with 2 N sodium 2-ethylhexoate in 4-methylpentan-2-one (1.4 ml) and diluted with ether to give sodium 7-(D,2-formyloxy-2-phenylacetamido)-3-(1-carbamoylmethyl-1H-tetrazol-5-ylthio)methylceph-3-em-4-carboxylate, 1.20 g, 43.5% yield; $\delta$[(CD$_3$)$_2$SO] 3.0–3.6 (2H,m, C$_2$ methylene), 3.9–4.6 (2H,m, —CH$_2$S—), 4.73 (1H,d, J5 Hz, C$_6$ proton), 5.02 (2H,s, —CH$_2$CO—), 5.3–5.8 (1H,m, C$_7$ proton), 6.15 (1H,s, PhCH<), 7.1–8.2 (7H,m, Ph— and —CONH$_2$), 8.32 (1H,s, —OCHO), 9.30 (1H,d, J 8 Hz, —CONH—).

(b)
7-(D,2-Hydroxy-2-phenylacetamido)-3-(1-carbamoylmethyl-1H-tetrazol-5-ylthio)methylceph-3-em-4-carboxylic acid The above product (1.20 g, 2 mmole) was added to an aqueous solution of sodium tetraborate decahydrate (1.53 g, 4 mmole) in water (25 ml), stirred at R.T. for three hours then worked up as in example 30a to give the sodium salt of the title compound, 0.20 g, 17.6% yield; $\delta$[(CD$_3$)$_2$SO] 3.4–3.7 (2H,m, C$_2$ methylene), 3.9–4.3 (2H,m, —CH$_2$S—), 4.8–5.2 (4H,m, C$_6$ proton, —CH$_2$CONH$_2$ and PhCH<), 5.5 and 5.8 (1H,m, C$_7$ proton), 7.0–7.9 (8H,m, Ph—, —OH and —CONH$_2$), 8.43 (1H,d, J 8 Hz, —CONH—).

EXAMPLE 31

7-(2-Methoxyimino-2-fur-2'-ylacetamido)-3-(1-carbamoylmethyl-1H-tetrazol-5-ylthio)methylceph-3-em-4-carboxylic acid 2-syn-Methoxyimino-2-fur-2'-ylacetyl chloride (6 mmole) was used to acylate 7-amino-3-(1-carbamoylmethyl-1H-tetrazol-5-ylthio)methylceph-3-em-4-carboxylate acid (1.86 g, 5 mmole) following the method described in example 30a to give a 47.8% yield of the sodium salt of the title compound; t.l.c. (SiO$_2$; B.A.W; 12:3:5) Rf=0.34; $\lambda$max (55% ethanol) 277 nm ($\epsilon$18,900); $\delta$(D$_2$O) 3.41 and 3.72 (2H, ABq, J 12 Hz, C$_2$ methylene), 3.96 (3H,s, —OCH$_3$), 4.09 and 4.33 (2H, ABq, J 11 Hz, —CH$_2$S—), 5.16 (1H,d, J 5 Hz, C$_6$ proton), 5.27 (2H, s, —CH$_2$CONH$_2$), 5.73 (1H,d, J 5 Hz, C$_7$ proton), 6.5–6.9 and 7.6–7.8 (3H,m, furyl protons).

EXAMPLE 32

7-[2-(4-Methylphenoxycarbonyl)-2-thien-3'-ylacetamido]-3-(1-carbamoylmethyl-1H-tetrazol-5-ylthio)methylceph-3-em-4-carboxylic acid 2-(4-Methylphenoxycarbonyl)-2-thien-3'-ylacetyl chloride (6 mmole) was used to acylate 7-amino-3-(1-carbamoylmethyl-1H-tetrazol-5-ylthio)methylceph-3-em-4-carboxylic acid (5 mmole) using the method described in example 30a to give the sodium salt of the title compound, 50.3% yield; t.l.c. (SiO$_2$; B.A.W; 12:3:5) Rf=0.40; $\delta$(D$_2$O) 2.15 (3H,s, —CH$_3$), 3.2–3.8 (2H,m, C$_2$ methylene), 3.9–4.4 (2H,m, —CH$_2$S—), 5.03 (1 H,d, J 5 Hz, C$_6$ proton), 5.20 (2H,s, —CH$_2$CONH$_2$), 5.5–5.7 (1H,m, C$_7$ proton), 6.58 and 6.99 (4H, ABq, J 8 Hz, aromatic protons), 7.0–7.6 (3H,m, thienyl protons).

EXAMPLE 33

7-(2-Carboxy-2-thien-3'-ylacetamido)-3-(1-carbamoylmethyl-1H-tetrazol-5-ylthio)methylceph-3-em-4-carboxylic acid Sodium 7-[2-(4-methylphenoxycarbonyl)-2-thien-3'-ylacetamido]-3-(1-carbamoylmethyl-1H-tetrazol-5-ylthio) methylceph-3-em-4-carboxylate (1.64 g) was added to sodium tetraborate decahydrate (1.92 g) in water (100 ml), stirred at R.T. for 3.5 hours, acidified to pH 4.0, washed with ethyl acetate (2×25 ml), acidified further to pH 1.8 and extracted with n-butanol (3×20 ml). The n-butanol extracts were washed with water (50 ml) and saturated brine (25 ml) dried, evaporated to dryness and the residue triturated with anhydrous ether to give the free acid, 0.50 g, which was dissolved in methanol (20 ml), treated with 2 N sodium 2-ethylhexoate in 4-methylpentan-2-one and diluted with ether to precipitate the sodium salt of the title compound. The solid was collected, washed with ether and dried, 0.47 g, 32.0% yield; t.l.c. (SiO; B.A.W; 12:3:5) Rf=0.25; $\delta$(D$_2$O) 3.1–3.8 (2H,m, C$_2$ methylene), 4.02 and 4.26 (2H, ABq, J 8 Hz, —CH$_2$S—), 4.9–5.1 (1H,m, C$_6$ proton), 5.22 (2H,s, —CH$_2$CONH$_2$), 5.5–5.7 (1H,m, C$_7$ proton), 7.0–7.5 (3H,m, thienyl protons).

EXAMPLE 34

7-[D,2-(4-Ethyl-2,3-dioxopiperazino-1-carbonylamino)-2-phenylacetamido]-3-(1-carbamoylmethyl-1H-tetrazol-5-ylthio)methylceph-3-em-4-carboxylic acid Sodium 7-[D,2-(4-ethyl-2,3-dioxopiperazino-1-carbonylamino)-2-phenylacetamido]-3-acetoxymethylceph-3-em-4-carboxylate (1.15 g, 2 mmole) and 5-mercapto-1H-tetrazol-5-ylacetamido (0.35 g; 2.2 mmole) in water (15 ml) were adjusted to pH 7.0 with sodium bicarbonate, heated at 60° for 7 hours, poured onto ice, washed with ethyl acetate (2×10 ml), acidified to pH 2.0 and extracted with n-butanol (3×15 ml). The extracts were washed with water (20 ml) and saturated brine (20 ml), dried, evaporated in vacuo and the residue triturated with anhydrous ether to give the title compound, 0.73 g. This in methanol (20 ml) was treated with 2 N sodium 2-ethylhexoate in 4-methylpentan-2-one (0.55 ml), diluted with anhydrous ether (50 ml) and the precipitated sodium salt collected, washed with ether and dried, 0.51 g, 37.6% yield; t.l.c. (SiO$_2$; B.A.W; 12:3:5) Rf=0.32; $\lambda$max (95% ethanol) 268 nm ($\epsilon$=8,580); $\delta$[(CD$_3$)$_2$SO] 1.10 (3H,t, J 7 Hz, —$CH_2\underline{CH_3}$), 2.9–3.8 (8H,m, piperazino and $C_2$ methylenes, >$N\underline{CH_2}CH_3$), 3.8–4.4 (2H,m, —$CH_2S$—), 4.93 (1H,d, J 5 Hz, $C_6$ proton), 5.08 (2H,s, —$\underline{CH_2}CONH_2$), 5.4–5.8 (2H,m, Ph$\underline{CH}$ and $C_7$ proton), 7.0–8.3 (7H,m, Ph— and —$CONH_2$), 9.41 (1H,d, J 8 Hz, —CONH—), 9.87, (1H,d, J 7 Hz, —CONH—).

EXAMPLE 35

(a)

7-Amino-3-(3-carbamoylmethyl-1,2,4-triazol-5-ylthio)-methylceph-3-em-4-carboxylic acid 7-ACA and 5-mercapto-1,2,4-triazol-3-ylacetamide were reacted as in example 23a to give the title compound, 58.4% yield; $\delta(CF_3CO_2H)$ 3.87 (2H, bs, $C_2$ methylene), 4.38 (2H,s, —$\underline{CH_2}CONH_2$), 4.55 (2H,bs, —$CH_2S$—), 5.40 (2H,s, β-lactam protons), 7.1–7.8 (2H,m, —$CONH_2$).

(b)

7-(2-Carboxy-2-thien-3'-ylacetamido)-3-(3-carbamoyl-methyl-1,2,4-triazol-5-ylthio)methylceph-3-em-4-carboxylic acid Thien-3-ylmalonic acid and 7-amino-3-(3-carbamoyl-methyl-1,2,4-triazol-5-ylthio)methylceph-3-em-4-carboxylic acid were coupled using the method described in Example 23b to give the sodium salt of the title compound, 27.1% yield; t.l.c. (SiO$_2$; B.A.W; 12:3:5) Rf=0.19; λmax (95% ethanol) 271 nm (ε=8,270); $\delta(D_2O)$ 3.55 (2H, bs, $C_2$ methylene), 3.80 (2H,s, —$\underline{CH_2}CONH_2$), 4.13 (2H,s, —$CH_2S$—), 4.9–5.2 (1H,m, $C_6$ proton), 5.5–5.8 (1H,m, $C_7$ proton), 7.0–7.6 (3H,m, thienyl protons).

What we claim is:

1. A compound pharmaceutically acceptable salt or in vivo hydrolysable carboxylic acid ester of the formula:

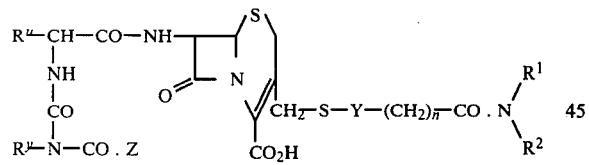

wherein $R^u$ is furyl, thienyl, cyclopropyl, cyclobutyl, cyclopentyl, cyclohexyl, cyclobutenyl, cyclopentenyl, cyclohexenyl or cyclohexa-1,4-dienyl, or phenyl, or phenyl substituted in the 4-position with hydroxy, or in the 3,4-positions with dihydroxy or by 3-halogen,-4-hydroxy, mono-nitro, lower alkyl, lower alkoxy, amino or carboxyl;

$R^y$ is hydrogen, lower alkyl or benzyl;

Z is methyl, ethyl, n- or iso-propyl, n-, sec- or tertbutyl, prop-2-enyl, but-2-enyl, benzyl, 2-phenylethyl, 3-phenylpropyl, p-chlorobenzyl, 2-(p-chlorophenyl)-ethyl, 2-phenylethenyl, 2-(p-nitrophenyl)ethenyl, 2-(p-chlorophenyl) ethenyl, phenyl, 2-methoxyphenyl, 2-chlorophenyl, 2-methoxyphenyl, 3,4,5-trimethoxyphenyl, 4-nitrophenyl, 2-methylphenyl, 4-methylphenyl, furyl, thienyl, or $R^y$ and Z together with the carbon and nitrogen atoms to which they are attached form a 5-, 6- or 7-membered ring selected from

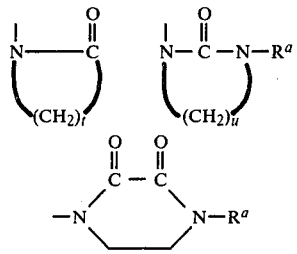

in which t is an integer from 3 to 5 and u is the integer from 2 to 4 and $R^a$ is hydrogen, $C_1$–$C_3$ alkyl, $C_1$–$C_3$ or $C_1$–$C_3$ alkylsulphonyl;

Y is diazolyl, triazolyl, tetrazolyl, thiazolyl, thiadiazolyl, thiatriazolyl, oxazolyl, or oxadiazolyl;

n is zero or 1, and $R^1$ and $R^2$ are the same or different and each is hydrogen or a $C_{1-6}$ alkyl group.

2. A compound as claimed in claim 1 wherein $R^u$ is 2- or 3-thienyl, phenyl or 4-hydroxyphenyl.

3. A compound as claimed in claim 1 wherein Y is oxadiazolyl, thiadiazolyl, or triazolyl.

4. A compound as claimed in claim 1 wherein Y is tetrazolyl.

5. A compound as claimed in claim 1 wherein n is 1.

6. A compound as claimed in claim 1 wherein $R^1$ and $R^2$ are both hydrogen.

7. A compound as claimed in claim 1 wherein Y is oxadiazol, thiadiazole or tetrazole and $R^u$ is phenyl or 4-hydroxyphenyl.

8. A compound as claimed in claim 7 selected from:
7-[D-α-(3-benzoyl-3-methylureido)-phenylacetamido]-3-(2-carbamoylmethyl-1,3,4-oxadiazol-5-ylthio)methylceph-3-em-4-carboxylic acid;
7-[D-α-(3-benzoyl-3-methylureido)-phenylacetamido]-3-(2-carbamoyl-1,3,4-oxadiazol-5-ylthio)methylceph-3-em-4-carboxylic acid;
7-[D-α-(3-benzoyl-3-methylureido)-phenylacetamido]-3-(1-carbamoylmethyl-1H-tetrazol-5-ylthio)methylceph-3-em-4-carboxylic acid;
7-[D,α-(3-benzoyl-3-methylureido)-phenylacetamido]-3-(2-carbamoylmethyl-1,3,4-thiadiazol-5-ylthio)methylceph-3-em-4-carboxylic acid;
7-[D-α-(3-2'-chlorobenzoyl-3-methylureido)-phenylacetamido]-3-(1-carbamoylmethyl-1H-tetrazol-5-ylthio)-methylceph-3-em-4-carboxylic acid;
7-[D-α-(3-2'-furoyl-3-methylureido)-phenylacetamido]-3-(1-carbamoylmethyl-1H-tetrazol-5-ylthio)methylceph-3-em-4-carboxylic acid;
7-[D-α-(3-isobutyryl-3-methylureido)-phenylacetamido]-3-(1-carbamoylmethyl-1H-tetrazol-5-ylthio)methylceph-3-em-4-carboxylic acid;
7-[D-α-(3-methyl-3-3'-thienoylureido)-phenylacetamido]-3-(1-carbamoylmethyl-1H-tetrazol-5-ylthio)methylceph-3-em-4-carboxylic acid;
7-[D-α-(3-3'-furoyl-3-methylureido)-phenylacetamido]-3-(1-carbamoylmethyl-1H-tetrazol-5-ylthio)methylceph-3-em-4-carboxylic acid;
7-[D,2(4-ethyl-2,3-dioxopiperazino-1-carbonylamino)-2-phenylacetamido]-3-(1-carbamoylmethyl-1H-tetrazol-5-ylthio)methylceph-3-em-4-carboxylic acid.

9. A compound as claimed in claim 1 wherein Y is tetrazolyl.

10. The compound of claim 1 which is 7-[D-α-(3-benzoyl-3-methylureido)phenylacetamido]-3-(1-carbamoylmethyl-1H-tetrazol-5-ylthio)methylceph-3-em-4-carboxylic acid.

11. The compound of claim 1 which is 7-[D-α-(3-2'-chlorobenzoyl-3-methylureido)phenylacetamido]-3-(1-carbamoylmethyl-1H-tetrazol-5-ylthio)-methylceph-3-em-4-carboxylic acid.

12. The compound of claim 1 which is 7-[D-α-(3-2'-furoyl-3-methylureido)phenylacetamido]-3-(1-carbamoylmethyl-1H-tetrazol-5-ylthio)methylceph-3-em-4-carboxylic acid.

13. The compound of claim 1 which is 7-[D-α-(3-isobutyryl-3-methylureido)phenylacetamido]-3-(1-carbamoylmethyl-1H-tetrazol-5-ylthio)methylceph-3-em-4-carboxylic acid.

14. The compound of claim 1 which is 7-[D-α-(3-methyl-3-3'-thienoylureido)phenylacetamido]-3-(1-carbamoylmethyl-1H-tetrazol-5-ylthio)methylceph-3-em-4-carboxylic acid.

15. The compound of claim 1 which is 7-[D-α-(3-3'-furoyl-3-methylureido)phenylacetamido]-3-(1-carbamoylmethyl-1H-tetrazol-5-ylthio)methylceph-3-em-4-carboxylic acid.

16. The compound of claim 1 which is 7-[D,2(4-ethyl-2,3-dioxopiperazino-1-carbonylamino)-2-phenylacetamido]-3-(1-carbamoylmethyl-1H-tetrazol-5-ylthio)methylceph-3-em-4-carboxylic acid.

17. An antibacterial pharmaceutical composition consisting essentially of an antibacterially effective amount of a compound of claim 1 together with a pharmaceutically acceptable carrier.

18. A composition as claimed in claim 17 which additionally incorporates a compound of formula (XVIII), or a pharmaceutically acceptable carboxylic acid salt or ester:

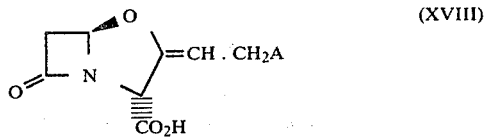

(XVIII)

wherein A is hydrogen or hydroxyl.

19. A composition as claimed in claim 18 wherein the compound of formula (XVIII) is clavulanic acid of formula (XIX) or a pharmaceutically acceptable carboxylic acid salt or ester:

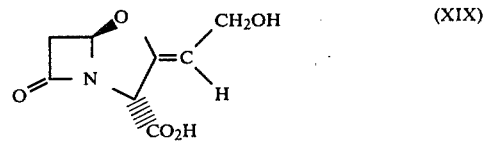

(XIX)

* * * * *